(12) United States Patent
Chin et al.

(10) Patent No.: US 7,303,560 B2
(45) Date of Patent: Dec. 4, 2007

(54) METHOD OF POSITIONING A MEDICAL INSTRUMENT

(75) Inventors: Sing Fatt Chin, Fremont, CA (US);
Dany Berube, Fremont, CA (US);
Dinesh I. Mody, Pleasanton, CA (US);
Nancy Norris, Fremont, CA (US)

(73) Assignee: AFx, Inc., Santa Clara, CA (US)

( * ) Notice: Subject to any disclaimer, the term of this patent is extended or adjusted under 35 U.S.C. 154(b) by 456 days.

(21) Appl. No.: 10/949,014

(22) Filed: Sep. 24, 2004

(65) Prior Publication Data
US 2006/0217694 A1 Sep. 28, 2006

Related U.S. Application Data

(63) Continuation of application No. 09/872,652, filed on Jun. 1, 2001, now Pat. No. 6,802,840, which is a continuation-in-part of application No. 09/751,472, filed on Dec. 29, 2000.

(51) Int. Cl.
*A61B 18/18* (2006.01)
*A61M 25/06* (2006.01)

(52) U.S. Cl. .......... 606/41; 606/45; 604/528; 600/146

(58) Field of Classification Search .......... 600/121, 600/123, 128, 143, 144, 146, 528, 585; 606/41, 606/46–50; 607/101–102
See application file for complete search history.

(56) References Cited

U.S. PATENT DOCUMENTS

| | | | |
|---|---|---|---|
| 1,586,645 A | 6/1926 | Bierman | |
| 3,598,108 A | 8/1971 | Jamshidi et al. | |
| 3,827,436 A | 8/1974 | Stumpf et al. | |
| 3,831,607 A | 8/1974 | Lindemann | |
| 3,886,944 A | 6/1975 | Jamshidi | |
| 3,976,082 A | 8/1976 | Schmitt | |
| 4,011,872 A | 3/1977 | Komiya | |
| 4,033,357 A | 7/1977 | Helland et al. | |
| 4,045,056 A | 8/1977 | Kandakov et al. | |

(Continued)

FOREIGN PATENT DOCUMENTS

EP  0048402 A1  3/1982

(Continued)

OTHER PUBLICATIONS

"Biopsy Needles Liver, Kidney and Soft Tissue Biopsy Menghini Technique Aspirating Needle Set," Popper & Sons, Inc., Biomedical Instrument Division.

(Continued)

*Primary Examiner*—Roy D. Gibson
(74) *Attorney, Agent, or Firm*—Fenwick & West LLP

(57) ABSTRACT

A system and method for positioning a medical instrument at a desired biological target tissue site is provided. The system includes an elongated sheath having a deflectable distal end configured to deflect or otherwise position at least a portion of a medical instrument during a surgical procedure allowing for the placement of the deflected portion adjacent or proximate to a predetermined target tissue surface. The positioning system may be incorporated into the medical instrument. The medical instrument may be an ablation system.

4 Claims, 18 Drawing Sheets

U.S. PATENT DOCUMENTS

| | | |
|---|---|---|
| 4,073,287 A | 2/1978 | Bradley et al. |
| 4,204,549 A | 5/1980 | Paglione |
| 4,244,371 A | 1/1981 | Farin |
| 4,245,624 A * | 1/1981 | Komiya ..................... 600/106 |
| 4,268,937 A | 5/1981 | Grimshaw |
| 4,312,364 A | 1/1982 | Convert et al. |
| 4,409,993 A | 10/1983 | Furihata |
| 4,416,276 A | 11/1983 | Newton et al. |
| 4,445,892 A | 5/1984 | Hussein et al. |
| 4,448,198 A | 5/1984 | Turner |
| 4,462,412 A | 7/1984 | Turner |
| 4,465,079 A | 8/1984 | Dickhudt |
| 4,476,872 A | 10/1984 | Perlin |
| 4,494,539 A | 1/1985 | Zenitani et al. |
| 4,522,212 A | 6/1985 | Gelinas et al. |
| 4,564,200 A | 1/1986 | Loring et al. |
| 4,565,200 A | 1/1986 | Cosman |
| 4,573,473 A | 3/1986 | Hess |
| 4,583,556 A | 4/1986 | Hines et al. |
| 4,601,296 A | 7/1986 | Yerushalmi |
| 4,611,604 A | 9/1986 | Botvidsson et al. |
| 4,640,983 A | 2/1987 | Comte |
| 4,641,646 A | 2/1987 | Schultz et al. |
| 4,641,649 A | 2/1987 | Walinsky et al. |
| 4,643,186 A | 2/1987 | Rosen et al. |
| 4,655,219 A | 4/1987 | Petruzzi |
| 4,657,015 A | 4/1987 | Irnich |
| 4,660,571 A | 4/1987 | Hess et al. |
| 4,681,122 A | 7/1987 | Winters et al. |
| 4,685,459 A | 8/1987 | Koch et al. |
| 4,699,147 A | 10/1987 | Chilson et al. |
| 4,700,716 A | 10/1987 | Kasevich et al. |
| 4,763,668 A | 8/1988 | Macek et al. |
| 4,785,815 A | 11/1988 | Cohen |
| 4,800,899 A | 1/1989 | Elliott |
| 4,823,812 A | 4/1989 | Eshel et al. |
| 4,825,880 A | 5/1989 | Stauffer et al. |
| 4,832,048 A | 5/1989 | Cohen |
| 4,841,988 A | 6/1989 | Fetter et al. |
| 4,841,990 A | 6/1989 | Kikuchi et al. |
| 4,881,543 A | 11/1989 | Trembly et al. |
| 4,891,483 A | 1/1990 | Kikuchi et al. |
| 4,920,978 A | 5/1990 | Colvin |
| 4,924,863 A | 5/1990 | Sterzer |
| 4,924,864 A | 5/1990 | Danzig |
| 4,932,420 A | 6/1990 | Goldstein |
| 4,938,217 A | 7/1990 | Lele |
| 4,945,912 A | 8/1990 | Langberg |
| 4,960,134 A | 10/1990 | Webster, Jr. |
| 4,966,597 A | 10/1990 | Cosman |
| 4,976,711 A | 12/1990 | Parins et al. |
| 5,007,437 A | 4/1991 | Sterzer |
| RE33,590 E | 5/1991 | Dory |
| 5,019,076 A | 5/1991 | Yamanashi et al. |
| 5,044,375 A | 9/1991 | Bach, Jr. et al. |
| 5,057,106 A | 10/1991 | Kasevich et al. |
| 5,078,713 A | 1/1992 | Varney |
| 5,080,101 A | 1/1992 | Dory |
| 5,080,102 A | 1/1992 | Dory |
| 5,085,659 A | 2/1992 | Rydell |
| 5,097,845 A | 3/1992 | Fetter et al. |
| 5,100,388 A | 3/1992 | Behl et al. |
| 5,104,393 A | 4/1992 | Isner et al. |
| 5,108,390 A | 4/1992 | Potocky et al. |
| 5,111,822 A | 5/1992 | Dory |
| 5,114,403 A | 5/1992 | Clarke et al. |
| 5,129,396 A | 7/1992 | Rosen et al. |
| 5,139,496 A | 8/1992 | Hed |
| 5,147,355 A | 9/1992 | Friedman et al. |
| 5,147,357 A | 9/1992 | Rose et al. |
| 5,150,717 A | 9/1992 | Rosen et al. |
| 5,156,151 A | 10/1992 | Imran |
| 5,158,092 A | 10/1992 | Glace |
| 5,171,255 A | 12/1992 | Rydell |
| 5,172,699 A | 12/1992 | Svenson et al. |
| 5,178,620 A | 1/1993 | Eggers et al. |
| 5,188,122 A | 2/1993 | Phipps et al. |
| 5,190,054 A | 3/1993 | Fetter et al. |
| 5,192,278 A | 3/1993 | Hayes et al. |
| 5,207,672 A | 5/1993 | Roth et al. |
| 5,207,674 A | 5/1993 | Hamilton |
| 5,222,501 A | 6/1993 | Ideker et al. |
| 5,230,334 A | 7/1993 | Klopotek |
| 5,230,349 A | 7/1993 | Langberg |
| 5,242,441 A | 9/1993 | Avitall |
| 5,246,438 A | 9/1993 | Langberg |
| 5,248,312 A | 9/1993 | Langberg |
| 5,263,493 A | 11/1993 | Avitall |
| 5,281,213 A | 1/1994 | Milder et al. |
| 5,281,215 A | 1/1994 | Milder |
| 5,281,217 A | 1/1994 | Edwards et al. |
| 5,293,869 A | 3/1994 | Edwards et al. |
| 5,295,484 A | 3/1994 | Marcus et al. |
| 5,295,955 A | 3/1994 | Rosen et al. |
| 5,300,068 A | 4/1994 | Rosar et al. |
| 5,300,099 A | 4/1994 | Rudie |
| 5,301,687 A | 4/1994 | Wong et al. |
| 5,304,207 A | 4/1994 | Stromer |
| 5,313,943 A | 5/1994 | Houser et al. |
| 5,314,466 A | 5/1994 | Stern et al. |
| 5,318,525 A | 6/1994 | West et al. |
| 5,323,781 A | 6/1994 | Ideker et al. |
| 5,327,889 A | 7/1994 | Imran |
| 5,334,168 A | 8/1994 | Hemmer |
| 5,341,807 A | 8/1994 | Nardella |
| 5,344,431 A | 9/1994 | Merritt et al. |
| 5,344,441 A | 9/1994 | Gronauer |
| 5,348,554 A | 9/1994 | Imran et al. |
| 5,358,515 A | 10/1994 | Hürter et al. |
| 5,364,336 A | 11/1994 | Carr |
| 5,364,351 A | 11/1994 | Heinzelman et al. |
| 5,364,352 A | 11/1994 | Cimino et al. |
| 5,364,392 A | 11/1994 | Warner et al. |
| 5,366,490 A | 11/1994 | Edwards et al. |
| 5,368,592 A | 11/1994 | Stern et al. |
| 5,369,251 A | 11/1994 | King et al. |
| 5,370,644 A | 12/1994 | Langberg |
| 5,370,675 A | 12/1994 | Edwards et al. |
| 5,370,677 A | 12/1994 | Rudie et al. |
| 5,370,678 A | 12/1994 | Edwards et al. |
| 5,374,287 A | 12/1994 | Rubin |
| 5,376,094 A | 12/1994 | Kline |
| 5,383,876 A | 1/1995 | Nardella |
| 5,383,922 A | 1/1995 | Zipes et al. |
| 5,391,147 A | 2/1995 | Imran et al. |
| 5,397,304 A | 3/1995 | Truckai |
| 5,398,683 A | 3/1995 | Edwards et al. |
| 5,402,772 A | 4/1995 | Moll et al. |
| 5,403,312 A | 4/1995 | Yates et al. |
| 5,405,346 A | 4/1995 | Grundy et al. |
| 5,405,375 A | 4/1995 | Ayers et al. |
| 5,405,376 A | 4/1995 | Mulier et al. |
| 5,415,656 A | 5/1995 | Tihon et al. |
| 5,417,208 A | 5/1995 | Winkler |
| 5,423,807 A | 6/1995 | Milder |
| 5,431,649 A | 7/1995 | Mulier et al. |
| 5,437,665 A | 8/1995 | Munro |
| 5,439,006 A | 8/1995 | Brennen et al. |
| 5,443,489 A | 8/1995 | Ben-Haim |
| 5,445,193 A | 8/1995 | Koeninger et al. |
| 5,450,846 A | 9/1995 | Goldreyer |
| 5,452,733 A | 9/1995 | Sterman et al. |
| 5,454,370 A | 10/1995 | Avitall |
| 5,454,733 A | 10/1995 | Watanabe et al. |

| | | | | | | |
|---|---|---|---|---|---|---|
| 5,454,807 A | 10/1995 | Lennox et al. | | 5,737,384 A | 4/1998 | Fenn |
| 5,462,544 A | 10/1995 | Saksena et al. | | 5,738,096 A | 4/1998 | Ben-Haim |
| 5,462,545 A | 10/1995 | Wang et al. | | 5,741,225 A | 4/1998 | Lax et al. |
| 5,464,404 A | 11/1995 | Abela et al. | | 5,741,249 A | 4/1998 | Moss et al. |
| 5,470,308 A | 11/1995 | Edwards et al. | | 5,743,239 A | 4/1998 | Iwase |
| 5,482,037 A | 1/1996 | Borghi | | 5,755,760 A | 5/1998 | Maguire et al. |
| 5,484,433 A | 1/1996 | Taylor et al. | | 5,762,066 A | 6/1998 | Law et al. |
| 5,487,757 A | 1/1996 | Truckai et al. | | 5,762,626 A | 6/1998 | Lundquist et al. |
| 5,492,126 A | 2/1996 | Hennige et al. | | 5,769,790 A | 6/1998 | Watkins et al. |
| 5,494,039 A | 2/1996 | Onik et al. | | 5,769,846 A | 6/1998 | Edwards et al. |
| 5,496,271 A | 3/1996 | Burton et al. | | 5,782,747 A | 7/1998 | Zimmon |
| 5,496,312 A | 3/1996 | Klicek | | 5,782,828 A | 7/1998 | Chen et al. |
| 5,500,012 A | 3/1996 | Brucker et al. | | 5,785,706 A | 7/1998 | Bednarek |
| 5,507,743 A | 4/1996 | Edwards et al. | | 5,785,707 A | 7/1998 | Boyd et al. |
| 5,514,131 A | 5/1996 | Edwards et al. | | 5,788,692 A | 8/1998 | Campbell et al. |
| 5,520,188 A | 5/1996 | Hennige et al. | | 5,797,905 A | 8/1998 | Fleischman et al. |
| 5,529,820 A | 6/1996 | Nomi et al. | | 5,797,960 A | 8/1998 | Stevens et al. |
| 5,531,677 A | 7/1996 | Lundquist et al. | | 5,800,378 A | 9/1998 | Edwards et al. |
| 5,536,247 A | 7/1996 | Thornton | | 5,800,379 A | 9/1998 | Edwards |
| 5,540,681 A | 7/1996 | Strul et al. | | 5,800,413 A | 9/1998 | Swartz et al. |
| 5,540,684 A | 7/1996 | Hassler, Jr. | | 5,800,428 A | 9/1998 | Nelson et al. |
| 5,545,193 A | 8/1996 | Fleischman et al. | | 5,800,482 A | 9/1998 | Pomeranz et al. |
| 5,545,200 A | 8/1996 | West et al. | | 5,800,494 A | 9/1998 | Campbell et al. |
| 5,549,638 A | 8/1996 | Burdette | | 5,807,309 A | 9/1998 | Lundquist et al. |
| 5,549,644 A | 8/1996 | Lundquist et al. | | 5,807,395 A | 9/1998 | Mulier et al. |
| 5,549,661 A | 8/1996 | Kordis et al. | | 5,810,803 A | 9/1998 | Moss et al. |
| 5,569,242 A | 10/1996 | Lax et al. | | 5,814,028 A | 9/1998 | Swartz et al. |
| 5,571,088 A | 11/1996 | Lennox et al. | | 5,823,197 A | 10/1998 | Edwards |
| 5,571,215 A | 11/1996 | Sterman et al. | | 5,823,955 A | 10/1998 | Kuck et al. |
| 5,575,766 A | 11/1996 | Swartz et al. | | 5,823,956 A | 10/1998 | Roth et al. |
| 5,575,810 A | 11/1996 | Swanson et al. | | 5,823,962 A | 10/1998 | Schaetzle et al. |
| 5,578,030 A | 11/1996 | Levin | | 5,826,576 A | 10/1998 | West |
| 5,578,067 A | 11/1996 | Ekwall et al. | | 5,827,216 A | 10/1998 | Igo et al. |
| 5,581,905 A | 12/1996 | Huelsman et al. | | 5,829,447 A | 11/1998 | Stevens et al. |
| 5,584,830 A | 12/1996 | Ladd et al. | | 5,836,947 A | 11/1998 | Fleischman et al. |
| 5,590,657 A | 1/1997 | Cain et al. | | 5,836,990 A | 11/1998 | Li |
| 5,593,404 A | 1/1997 | Costello et al. | | 5,840,027 A | 11/1998 | Swartz et al. |
| 5,593,405 A | 1/1997 | Osypka | | 5,840,030 A | 11/1998 | Ferek-Petric et al. |
| 5,599,295 A | 2/1997 | Rosen et al. | | 5,842,037 A | 11/1998 | Haartsen |
| 5,599,346 A | 2/1997 | Baker et al. | | 5,843,026 A | 12/1998 | Edwards et al. |
| 5,603,697 A | 2/1997 | Grundy et al. | | 5,843,075 A | 12/1998 | Taylor |
| 5,606,974 A | 3/1997 | Castellano et al. | | 5,843,171 A | 12/1998 | Campbell et al. |
| 5,607,389 A | 3/1997 | Edwards et al. | | 5,846,238 A | 12/1998 | Jackson et al. |
| 5,628,771 A | 5/1997 | Mizukawa et al. | | 5,852,860 A | 12/1998 | Lorraine et al. |
| 5,630,837 A | 5/1997 | Crowley | | 5,853,366 A | 12/1998 | Dowlatshahi |
| 5,640,955 A | 6/1997 | Ockuly et al. | | 5,853,368 A | 12/1998 | Solomon et al. |
| 5,643,255 A | 7/1997 | Organ | | 5,855,614 A | 1/1999 | Stevens et al. |
| 5,658,280 A | 8/1997 | Issa | | 5,860,920 A | 1/1999 | McGee et al. |
| 5,672,172 A | 9/1997 | Zupkas | | 5,861,002 A | 1/1999 | Desai |
| 5,672,174 A | 9/1997 | Gough et al. | | 5,861,021 A | 1/1999 | Thome et al. |
| 5,673,694 A | 10/1997 | Rivers | | 5,863,290 A | 1/1999 | Gough et al. |
| 5,673,695 A | 10/1997 | McGee et al. | | 5,868,737 A | 2/1999 | Taylor et al. |
| 5,676,692 A | 10/1997 | Sanghvi et al. | | 5,871,481 A | 2/1999 | Kannenberg et al. |
| 5,676,693 A | 10/1997 | LaFontaine | | 5,871,525 A | 2/1999 | Edwards et al. |
| 5,681,308 A | 10/1997 | Edwards et al. | | 5,873,828 A | 2/1999 | Fujio et al. |
| 5,683,382 A | 11/1997 | Lenihan et al. | | 5,873,896 A | 2/1999 | Ideker |
| 5,683,384 A | 11/1997 | Gough et al. | | 5,882,302 A | 3/1999 | Driscoll, Jr. et al. |
| 5,687,723 A | 11/1997 | Avitall | | 5,885,278 A | 3/1999 | Fleischman |
| 5,688,267 A | 11/1997 | Panescu et al. | | 5,895,355 A | 4/1999 | Schaer |
| 5,693,078 A | 12/1997 | Desai et al. | | 5,897,553 A | 4/1999 | Mulier et al. |
| 5,693,082 A | 12/1997 | Warner et al. | | 5,897,554 A | 4/1999 | Chia et al. |
| 5,694,701 A | 12/1997 | Huelsman et al. | | 5,899,899 A | 5/1999 | Arless et al. |
| 5,697,928 A | 12/1997 | Walcott et al. | | 5,904,709 A | 5/1999 | Arndt et al. |
| 5,707,369 A | 1/1998 | Vaitekunas et al. | | 5,906,580 A | 5/1999 | Kline-Schoder et al. |
| 5,718,226 A | 2/1998 | Riza | | 5,910,129 A | 6/1999 | Koblish et al. |
| 5,718,241 A | 2/1998 | Ben-Haim et al. | | 5,916,213 A | 6/1999 | Haissaguerre et al. |
| 5,720,718 A | 2/1998 | Rosen et al. | | 5,919,188 A | 7/1999 | Shearon et al. |
| 5,720,775 A | 2/1998 | Larnard | | 5,921,924 A | 7/1999 | Avitall |
| 5,725,523 A | 3/1998 | Mueller | | 5,924,424 A | 7/1999 | Stevens et al. |
| 5,730,127 A | 3/1998 | Avitall | | 5,931,810 A | 8/1999 | Grabek |
| 5,733,280 A | 3/1998 | Avitall | | 5,938,600 A | 8/1999 | Van Vaals et al. |
| 5,733,281 A | 3/1998 | Nardella | | 5,938,612 A | 8/1999 | Kline-Schoder et al. |
| 5,735,280 A | 4/1998 | Sherman et al. | | 5,938,692 A | 8/1999 | Rudie |

| Patent No. | Date | Inventor |
|---|---|---|
| 5,954,662 A | 9/1999 | Swanson et al. |
| 5,954,665 A | 9/1999 | Ben-Haim |
| 5,957,842 A | 9/1999 | Littmann et al. |
| 5,957,969 A | 9/1999 | Warner et al. |
| 5,964,727 A | 10/1999 | Edwards et al. |
| 5,964,732 A | 10/1999 | Willard |
| 5,964,756 A | 10/1999 | McGaffigan et al. |
| 5,971,983 A | 10/1999 | Lesh |
| 5,978,714 A | 11/1999 | Zadini et al. |
| 5,980,697 A | 11/1999 | Kolb et al. |
| 5,993,389 A | 11/1999 | Driscoll, Jr. et al. |
| 5,993,445 A | 11/1999 | Issa |
| 5,993,447 A | 11/1999 | Blewett et al. |
| 5,995,875 A | 11/1999 | Blewett et al. |
| 6,002,955 A | 12/1999 | Willems et al. |
| 6,004,269 A | 12/1999 | Crowley et al. |
| 6,007,499 A | 12/1999 | Martin et al. |
| 6,010,516 A | 1/2000 | Hulka |
| 6,012,457 A | 1/2000 | Lesh |
| 6,016,811 A | 1/2000 | Knopp et al. |
| 6,016,848 A | 1/2000 | Egres, Jr. |
| 6,024,740 A | 2/2000 | Lesh et al. |
| 6,027,497 A | 2/2000 | Daniel et al. |
| 6,027,501 A | 2/2000 | Goble et al. |
| 6,030,382 A | 2/2000 | Fleischman et al. |
| 6,032,077 A | 2/2000 | Pomeranz |
| 6,056,735 A | 5/2000 | Okada et al. |
| 6,056,743 A | 5/2000 | Ellis et al. |
| 6,059,778 A | 5/2000 | Sherman |
| 6,063,077 A | 5/2000 | Schaer |
| 6,063,081 A | 5/2000 | Mulier et al. |
| 6,064,902 A | 5/2000 | Haissaguerre et al. |
| 6,066,094 A | 5/2000 | Ben-Haim |
| 6,068,628 A | 5/2000 | Fanton et al. |
| 6,068,629 A | 5/2000 | Haissaguerre et al. |
| 6,071,274 A | 6/2000 | Thompson et al. |
| 6,071,281 A | 6/2000 | Burnside et al. |
| 6,076,012 A | 6/2000 | Swanson et al. |
| 6,083,159 A | 7/2000 | Driscoll, Jr. et al. |
| 6,086,583 A | 7/2000 | Ouchi |
| 6,090,104 A | 7/2000 | Webster, Jr. |
| 6,090,105 A | 7/2000 | Zepeda et al. |
| 6,097,985 A | 8/2000 | Kasevich et al. |
| 6,102,886 A | 8/2000 | Lundquist et al. |
| 6,106,517 A | 8/2000 | Zupkas |
| 6,106,521 A | 8/2000 | Blewett et al. |
| 6,106,522 A | 8/2000 | Fleischman et al. |
| 6,106,524 A | 8/2000 | Eggers et al. |
| 6,117,101 A | 9/2000 | Diederich et al. |
| 6,119,041 A | 9/2000 | Pomeranz et al. |
| 6,135,971 A | 10/2000 | Hutchinson et al. |
| 6,142,994 A | 11/2000 | Swanson et al. |
| 6,146,378 A | 11/2000 | Mikus et al. |
| 6,146,379 A | 11/2000 | Fleischman et al. |
| 6,152,920 A | 11/2000 | Thompson et al. |
| 6,161,543 A | 12/2000 | Cox et al. |
| 6,162,216 A | 12/2000 | Guziak et al. |
| 6,164,283 A | 12/2000 | Lesh |
| 6,165,174 A | 12/2000 | Jacobs et al. |
| 6,171,303 B1 | 1/2001 | Ben-Haim et al. |
| 6,174,309 B1 | 1/2001 | Wrublewski et al. |
| 6,178,354 B1 | 1/2001 | Gibson |
| 6,179,776 B1 * | 1/2001 | Adams et al. ............ 600/121 |
| 6,182,664 B1 | 2/2001 | Cosgrove |
| 6,190,382 B1 | 2/2001 | Ormsby et al. |
| 6,200,315 B1 | 3/2001 | Gaiser et al. |
| 6,206,831 B1 | 3/2001 | Suorsa et al. |
| 6,210,356 B1 | 4/2001 | Anderson et al. |
| 6,216,027 B1 | 4/2001 | Willis et al. |
| 6,217,530 B1 | 4/2001 | Martin et al. |
| 6,217,573 B1 | 4/2001 | Webster |
| 6,224,587 B1 | 5/2001 | Gibson |
| 6,231,518 B1 | 5/2001 | Grabek et al. |
| 6,233,490 B1 | 5/2001 | Kasevich |
| 6,235,025 B1 | 5/2001 | Swartz et al. |
| 6,235,796 B1 | 5/2001 | Niazi |
| 6,237,605 B1 | 5/2001 | Vaska et al. |
| 6,241,722 B1 | 6/2001 | Dobak et al. |
| 6,241,728 B1 | 6/2001 | Gaiser et al. |
| 6,241,754 B1 | 6/2001 | Swanson et al. |
| 6,245,062 B1 | 6/2001 | Berube et al. |
| 6,251,128 B1 | 6/2001 | Knopp et al. |
| 6,273,887 B1 | 8/2001 | Yamauchi et al. |
| 6,277,113 B1 | 8/2001 | Berube |
| 6,283,955 B1 | 9/2001 | Pacala et al. |
| 6,287,302 B1 | 9/2001 | Berube |
| 6,289,249 B1 | 9/2001 | Arndt et al. |
| 6,290,699 B1 | 9/2001 | Hall et al. |
| 6,302,880 B1 | 10/2001 | Schaer |
| 6,306,124 B1 | 10/2001 | Jones et al. |
| 6,306,132 B1 | 10/2001 | Moorman et al. |
| 6,309,388 B1 | 10/2001 | Fowler |
| 6,311,692 B1 | 11/2001 | Vaska et al. |
| 6,312,425 B1 | 11/2001 | Simpson et al. |
| 6,312,427 B1 | 11/2001 | Berube et al. |
| 6,314,962 B1 | 11/2001 | Vaska et al. |
| 6,314,963 B1 | 11/2001 | Vaska et al. |
| 6,315,741 B1 | 11/2001 | Martin et al. |
| 6,322,558 B1 | 11/2001 | Taylor et al. |
| 6,325,796 B1 | 12/2001 | Berube et al. |
| 6,325,797 B1 | 12/2001 | Stewart et al. |
| 6,332,881 B1 | 12/2001 | Carner et al. |
| 6,346,104 B2 | 2/2002 | Daly et al. |
| 6,355,033 B1 | 3/2002 | Moorman et al. |
| 6,356,790 B1 | 3/2002 | Maguire et al. |
| 6,358,248 B1 | 3/2002 | Mulier et al. |
| 6,361,531 B1 | 3/2002 | Hissong |
| 6,364,876 B1 | 4/2002 | Erb et al. |
| 6,379,348 B1 | 4/2002 | Onik |
| 6,383,182 B1 | 5/2002 | Berube et al. |
| 6,402,556 B1 | 6/2002 | Lang et al. |
| 6,413,254 B1 | 7/2002 | Hissong et al. |
| 6,423,057 B1 | 7/2002 | He et al. |
| 6,423,059 B1 | 7/2002 | Hanson et al. |
| 6,428,538 B1 | 8/2002 | Blewett et al. |
| 6,430,426 B2 | 8/2002 | Avitall |
| 6,432,067 B1 | 8/2002 | Martin et al. |
| 6,432,069 B1 | 8/2002 | Godo et al. |
| 6,433,464 B2 | 8/2002 | Jones |
| 6,454,758 B1 | 9/2002 | Thompson et al. |
| 6,461,314 B1 | 10/2002 | Pant et al. |
| 6,464,700 B1 | 10/2002 | Koblish et al. |
| 6,467,138 B1 | 10/2002 | Aimé |
| 6,471,696 B1 | 10/2002 | Berube et al. |
| 6,471,697 B1 | 10/2002 | Lesh |
| 6,474,340 B1 | 11/2002 | Vaska et al. |
| 6,475,179 B1 | 11/2002 | Wang et al. |
| 6,484,727 B1 | 11/2002 | Vaska et al. |
| 6,488,639 B1 | 12/2002 | Ribault et al. |
| 6,488,679 B1 | 12/2002 | Swanson et al. |
| 6,488,680 B1 | 12/2002 | Francischelli et al. |
| 6,490,474 B1 | 12/2002 | Willis et al. |
| 6,500,133 B2 | 12/2002 | Martin et al. |
| 6,502,575 B1 | 1/2003 | Jacobs et al. |
| 6,508,774 B1 | 1/2003 | Acker et al. |
| 6,511,478 B1 | 1/2003 | Burnside et al. |
| 6,514,246 B1 | 2/2003 | Swanson et al. |
| 6,514,249 B1 | 2/2003 | Maguire et al. |
| 6,517,536 B2 | 2/2003 | Hooven et al. |
| 6,517,568 B1 | 2/2003 | Sharkey et al. |
| 6,526,320 B2 | 2/2003 | Mitchell |
| 6,527,767 B2 | 3/2003 | Wang et al. |
| 6,527,768 B2 | 3/2003 | Berube |
| 6,529,756 B1 | 3/2003 | Phan et al. |
| 6,533,780 B1 | 3/2003 | Laird et al. |
| 6,542,781 B1 | 4/2003 | Koblish et al. |

| | | |
|---|---|---|
| 6,546,935 B2 | 4/2003 | Hooven |
| 6,558,375 B1 | 5/2003 | Sinofsky et al. |
| 6,576,875 B1 | 6/2003 | Kleffner et al. |
| 6,584,360 B2 | 6/2003 | Francischelli et al. |
| 6,586,040 B1 | 7/2003 | von Falkenhausen |
| 6,602,224 B1 | 8/2003 | Simhambhatla |
| 6,610,055 B1 | 8/2003 | Swanson et al. |
| 6,645,200 B1 | 11/2003 | Koblish et al. |
| 6,645,202 B1 | 11/2003 | Pless et al. |
| 6,648,883 B2 | 11/2003 | Francischelli et al. |
| 6,652,513 B2 | 11/2003 | Panescu et al. |
| 6,663,622 B1 | 12/2003 | Foley et al. |
| 6,663,627 B2 | 12/2003 | Francischelli et al. |
| 6,673,068 B1 | 1/2004 | Berube |
| 6,685,715 B2 | 2/2004 | Danitz et al. |
| 6,689,062 B1 | 2/2004 | Mesallum |
| 6,689,128 B2 | 2/2004 | Sliwa, Jr. et al. |
| 6,692,491 B1 | 2/2004 | Phan |
| 6,696,844 B2 | 2/2004 | Wong et al. |
| 6,699,240 B2 | 3/2004 | Francischelli |
| 6,701,931 B2 | 3/2004 | Sliwa, Jr. et al. |
| 6,706,038 B2 | 3/2004 | Francischelli et al. |
| 6,719,755 B2 | 4/2004 | Sliwa, Jr. et al. |
| 6,723,092 B2 | 4/2004 | Brown et al. |
| 6,740,080 B2 | 5/2004 | Jain et al. |
| 6,743,225 B2 | 6/2004 | Sanchez et al. |
| 6,761,716 B2 | 7/2004 | Kadhiresan et al. |
| 6,802,840 B2 | 10/2004 | Chin et al. |
| 6,805,709 B1 | 10/2004 | Schaldach et al. |
| 6,805,898 B1 | 10/2004 | Wu et al. |
| 6,807,968 B2 | 10/2004 | Francischelli et al. |
| 6,808,483 B1 | 10/2004 | Ortiz et al. |
| 6,808,484 B1 | 10/2004 | Peters et al. |
| 6,808,529 B2 | 10/2004 | Fulkerson |
| 6,808,536 B2 | 10/2004 | Wright et al. |
| 6,808,739 B2 | 10/2004 | Sitz et al. |
| 2001/0031961 A1 | 10/2001 | Hooven |
| 2001/0039416 A1 | 11/2001 | Moorman et al. |
| 2002/0001655 A1 | 1/2002 | Kuechle et al. |
| 2002/0017306 A1 | 2/2002 | Cox et al. |
| 2002/0032440 A1 | 3/2002 | Hooven et al. |
| 2002/0042610 A1 | 4/2002 | Sliwa, Jr. et al. |
| 2002/0042611 A1 | 4/2002 | Sliwa et al. |
| 2002/0045895 A1 | 4/2002 | Sliwa, Jr. et al. |
| 2002/0058932 A1 | 5/2002 | Moorman et al. |
| 2002/0087151 A1 | 7/2002 | Mody et al. |
| 2002/0087157 A1 | 7/2002 | Sliwa, Jr. et al. |
| 2002/0091382 A1 | 7/2002 | Hooven |
| 2002/0091383 A1 | 7/2002 | Hooven |
| 2002/0091384 A1 | 7/2002 | Hooven et al. |
| 2002/0095145 A1 | 7/2002 | Holzapfel et al. |
| 2002/0103484 A1 | 8/2002 | Hooven |
| 2002/0107513 A1 | 8/2002 | Hooven |
| 2002/0107514 A1 | 8/2002 | Hooven |
| 2002/0111613 A1 | 8/2002 | Berube |
| 2002/0115993 A1 | 8/2002 | Hooven |
| 2002/0120263 A1 | 8/2002 | Brown et al. |
| 2002/0120267 A1 | 8/2002 | Phan |
| 2002/0120316 A1 | 8/2002 | Hooven et al. |
| 2002/0128639 A1 | 9/2002 | Pless et al. |
| 2002/0128642 A1 | 9/2002 | Berube et al. |
| 2002/0173784 A1 | 11/2002 | Sliwa, Jr. et al. |
| 2002/0193783 A1 | 12/2002 | Gauthier et al. |
| 2002/0193786 A1 | 12/2002 | Berube et al. |
| 2003/0004507 A1 | 1/2003 | Francischelli |
| 2003/0014046 A1 | 1/2003 | Edwards et al. |
| 2003/0024537 A1 | 2/2003 | Cox et al. |
| 2003/0028187 A1 | 2/2003 | Vaska et al. |
| 2003/0029462 A1 | 2/2003 | Cox et al. |
| 2003/0032952 A1 | 2/2003 | Hooven |
| 2003/0050630 A1 | 3/2003 | Mody et al. |
| 2003/0050631 A1 | 3/2003 | Mody et al. |
| 2003/0069574 A1 | 4/2003 | Sliwa, Jr. et al. |
| 2003/0069575 A1 | 4/2003 | Fatt et al. |
| 2003/0069577 A1 | 4/2003 | Vaska et al. |
| 2003/0073988 A1 | 4/2003 | Berube et al. |
| 2003/0073992 A1 | 4/2003 | Sliwa, Jr. et al. |
| 2003/0078571 A1 | 4/2003 | Sliwa, Jr. et al. |
| 2003/0079753 A1 | 5/2003 | Vaska et al. |
| 2003/0083654 A1 | 5/2003 | Fatt et al. |
| 2003/0093068 A1 | 5/2003 | Hooven |
| 2003/0097126 A1 | 5/2003 | Woloszko et al. |
| 2003/0109868 A1 | 6/2003 | Fatt et al. |
| 2003/0125725 A1 | 7/2003 | Woodard et al. |
| 2003/0125729 A1 | 7/2003 | Hooven et al. |
| 2003/0163128 A1 | 8/2003 | Patil et al. |
| 2003/0171745 A1 | 9/2003 | Francischelli et al. |
| 2003/0176764 A1 | 9/2003 | Fiegel et al. |
| 2004/0049179 A1 | 3/2004 | Francischelli et al. |
| 2004/0106918 A1 | 6/2004 | Cox et al. |

FOREIGN PATENT DOCUMENTS

| | | |
|---|---|---|
| EP | 0139607 A1 | 5/1985 |
| EP | 0248758 A1 | 12/1987 |
| EP | 0358 336 A1 | 3/1990 |
| EP | 0628322 A2 | 12/1994 |
| EP | 0655 225 B1 | 3/2000 |
| EP | 0738501 B1 | 5/2000 |
| EP | 1005838 A1 | 6/2000 |
| EP | 1042990 A1 | 10/2000 |
| EP | 1118310 A1 | 7/2001 |
| EP | 0839547 B1 | 9/2003 |
| WO | WO93/08757 | 5/1993 |
| WO | WO93/15664 | 8/1993 |
| WO | WO93/20767 | 10/1993 |
| WO | WO93/20768 | 10/1993 |
| WO | WO93/20886 | 10/1993 |
| WO | WO93/20893 | 10/1993 |
| WO | WO 93/24065 | 12/1993 |
| WO | WO94/02204 | 2/1994 |
| WO | WO 95/05212 | 2/1995 |
| WO | WO 00/16850 | 5/1995 |
| WO | WO 95/18575 | 7/1995 |
| WO | WO 96/26675 | 9/1996 |
| WO | WO 96/35469 A1 | 11/1996 |
| WO | WO96/36397 | 11/1996 |
| WO | WO97/42893 | 11/1997 |
| WO | WO 97/44092 A | 11/1997 |
| WO | WO98/06341 | 2/1998 |
| WO | WO98/17185 | 4/1998 |
| WO | WO98/17187 | 4/1998 |
| WO | WO98/44857 | 10/1998 |
| WO | WO 99/04696 | 2/1999 |
| WO | WO99/08613 | 2/1999 |
| WO | WO99/34860 | 7/1999 |
| WO | WO 99/59486 | 11/1999 |
| WO | WO00/24463 | 5/2000 |
| WO | WO00/35363 | 6/2000 |
| WO | WO00/56239 | 9/2000 |
| WO | WO01/05306 A1 | 1/2001 |
| WO | WO 01/15616 A1 | 3/2001 |
| WO | WO 01/41664 A | 6/2001 |
| WO | WO01/58373 A1 | 8/2001 |
| WO | WO 01/80755 A2 | 11/2001 |
| WO | WO 01/82814 A2 | 11/2001 |
| WO | WO02/01655 A2 | 1/2002 |
| WO | WO 02/05722 A1 | 1/2002 |
| WO | WO02/38052 A2 | 5/2002 |
| WO | WO 02/060523 A2 | 8/2002 |

OTHER PUBLICATIONS

Andriole et al., "Biopsy Needle Characteristics Assessed in the Laboratory," Radiology, vol. 148, No. 3, Sep. 1983, pp. 659-662.

Arendt-Nielsen et al., "Selectivity of Spatial Filters for Surface EMG Detection from the Tibialis Anterior Muscle," [online], © 200

[retrieved Nov. 23, 2003], 2 pages, Retrieved from the Internet: <URL:http://www.lisin.polito.it/english/annual_reports/ar2002_uk/19uk.htm.

Cheng, "Field and Wave Electromagnetics," 1989, Addison Wesley Publishing Co., Inc., pp. 485-509.

Cox, "The Surgical Treatment of Atrial Fibrillation IV Surgical Technique," J Thorac Cardiovasc. Surg. 101, 1991, pp. 584-592.

Durney et al., "Antennas for Medical Applications" Chapter 24, pp. 24-2, 24-27, 24-28, 24-29 and 24-58.

Gottlieb et al., "Interstitial Microwave Hyperthermia Applicators Having Submillimetre Diameters," Int. J. Hyperthermia, vol. 6, No. 3, 1990, pp. 707-714.

Haines et al., "Tissue Heating During Radiofrequency Catheter Ablation: A Thermodynamic Model and Observation in Isolated Perfused and Superfused Canine Right Ventricular Free Wall," Pacint Clin Electrophysol, Jun. 1989, 12(6), pp. 962-976.

Knaut et al., "Interoperative Microwave Ablation for Curative Treatment of Atrial Fibrillation in Open Heart Surgery—The MICRO-STAF and MICRO-PASS Pilot Trial," Thorac.Cardiovasc. Surg. 47 (Supplement), 1999, pp. 379-384.

Labonte et al., "Monopole Antennas for Microwave Catheter Ablation," IEEE Transactions on Microwave Theory and Techniques, vol. 44, No. 10, Oct. 1996, pp. 1832-1840.

Langberg et al., "Catheter Ablation of the Atrioventricular Junction Using a Helical Microwave Antenna: A Novel Means of Coupling Energy to Endocardium," Pace, vol. 14, Dec. 1991, pp. 2105-2113.

Liem et al., "Microwave Linear Ablation of the Isthmus Between the Inferior Vena Cava and Tricuspid Annulus," Pace, vol. 21, Nov. 1998, pp. 2079-2086.

Matsukawa et al., "Precutaneous Microwave Coagulation Therapy In Liver Tumors: A 3-Year Experience," Acta Radiologica, vol. 38, 1997, pp. 410-415.

Murakami et al., "Treatment of Hepatocellular Carcinoma: Value of Percutaneous Microwave Coagulation," American Journal of Roentgenology, vol. 164, No. 5, May 1995, pp. 1159-1164.

Sato et al., "Microwave Coagulation Therapy for Hepatocellular Carcinoma," Gastroenterology, vol. 110, No. 5, May 1996, pp. 1507-1514.

Sato et al., "Two Long-Term Survivors After Microwave Coagulation Therapy for Hepatocellular Carcinoma: A Case Report,", Hepatogastroenterology, vol. 43, No. 10, Jul. 1996, pp. 1035-1039.

Seki et al., "Ultrasonically Guided Percutaneous Microwave Coagulation Therapy for Small Hepatocellular Carcinoma," Cancer, vol. 74, No. 3, Aug. 1, 1994, pp. 817-825.

* cited by examiner

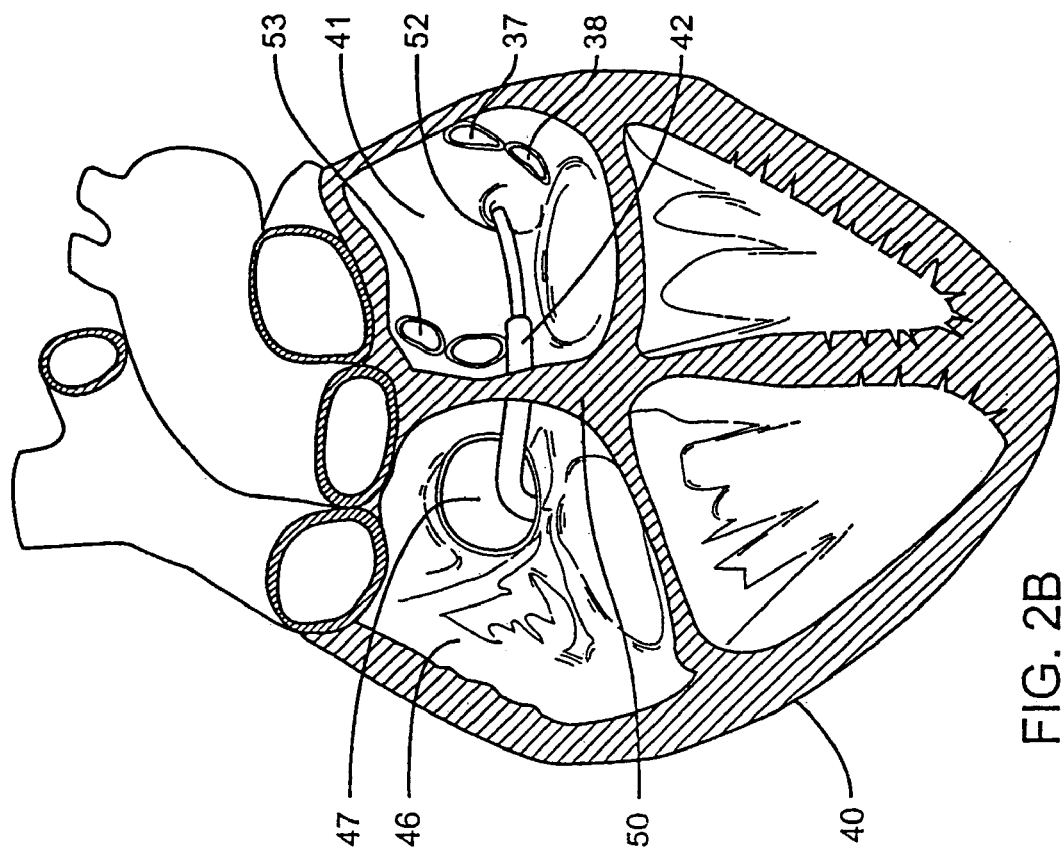
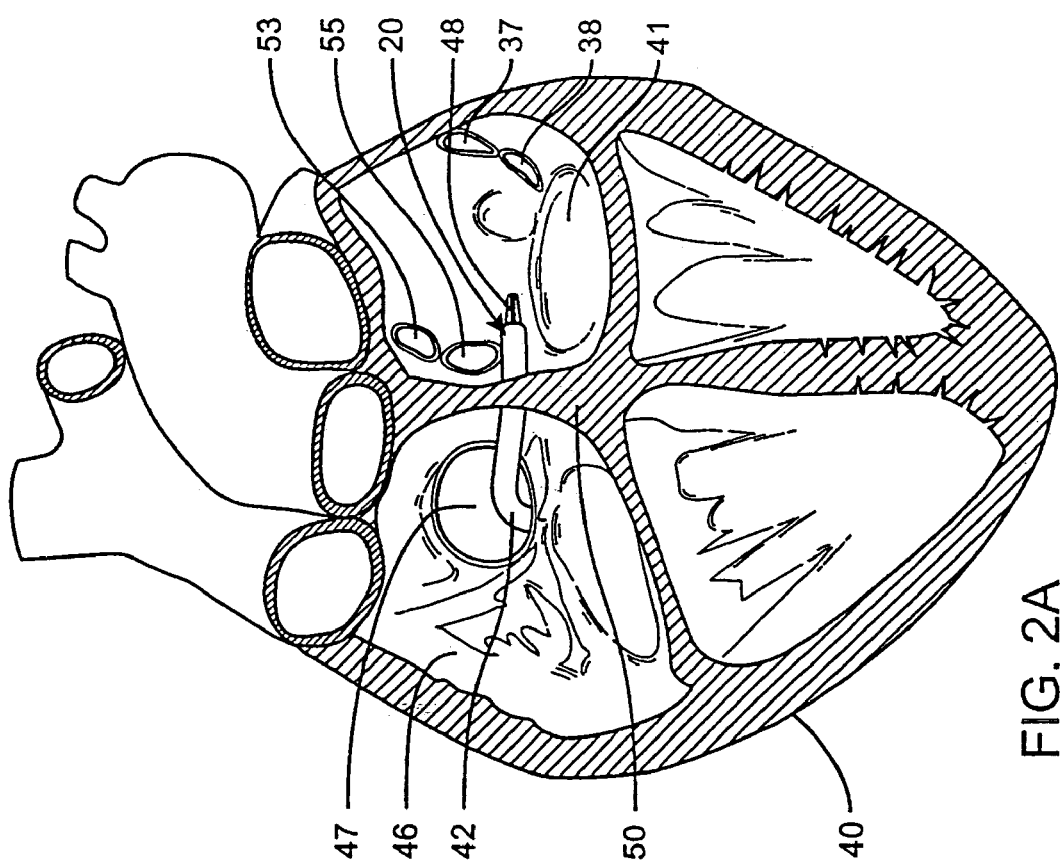

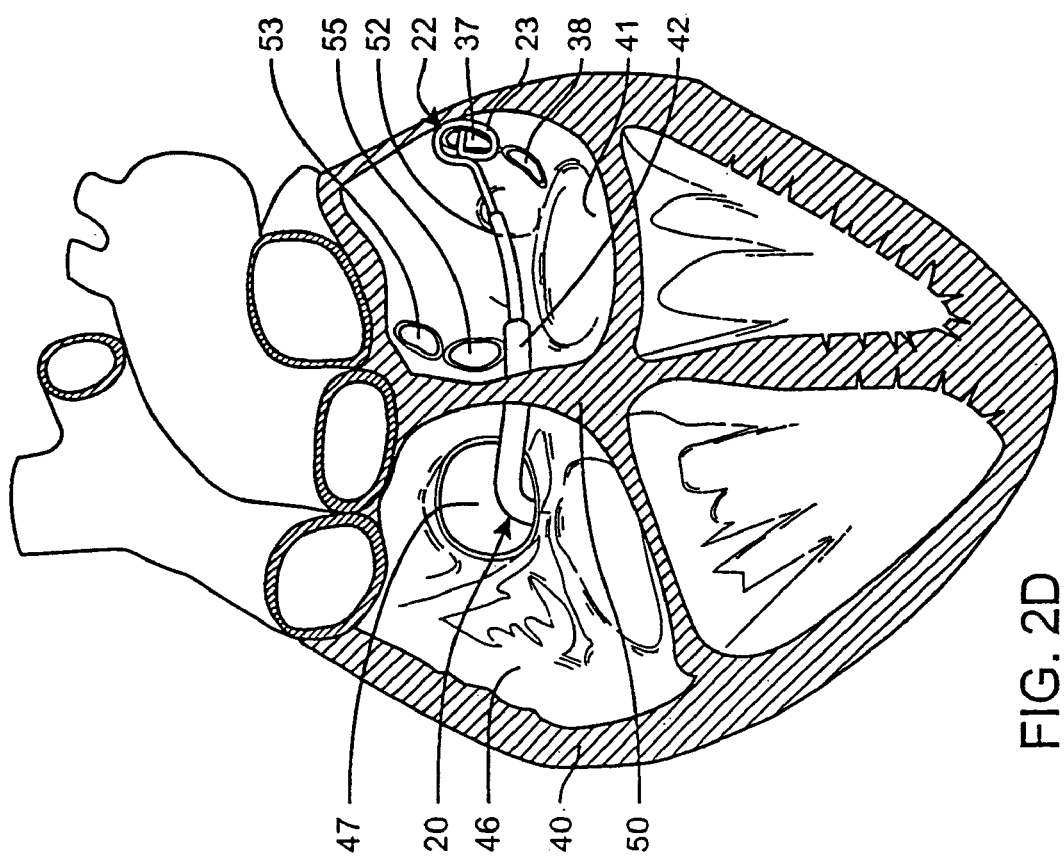
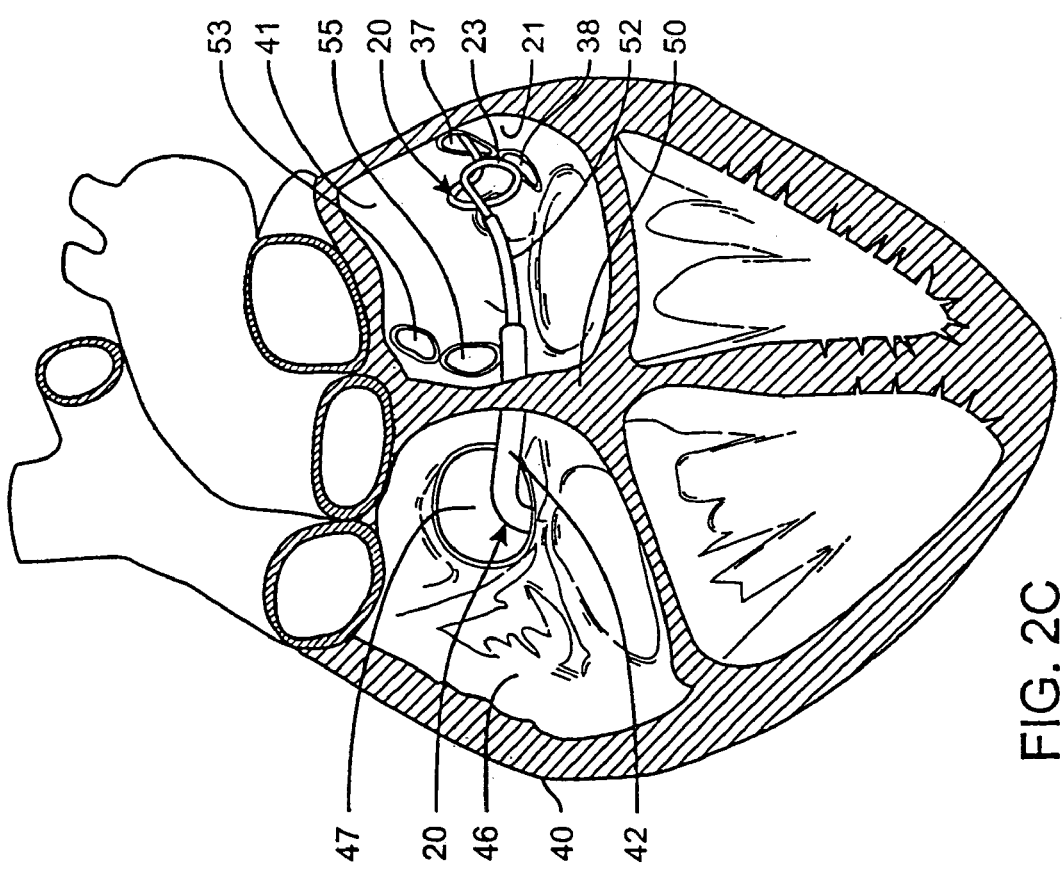
FIG. 2C
FIG. 2D

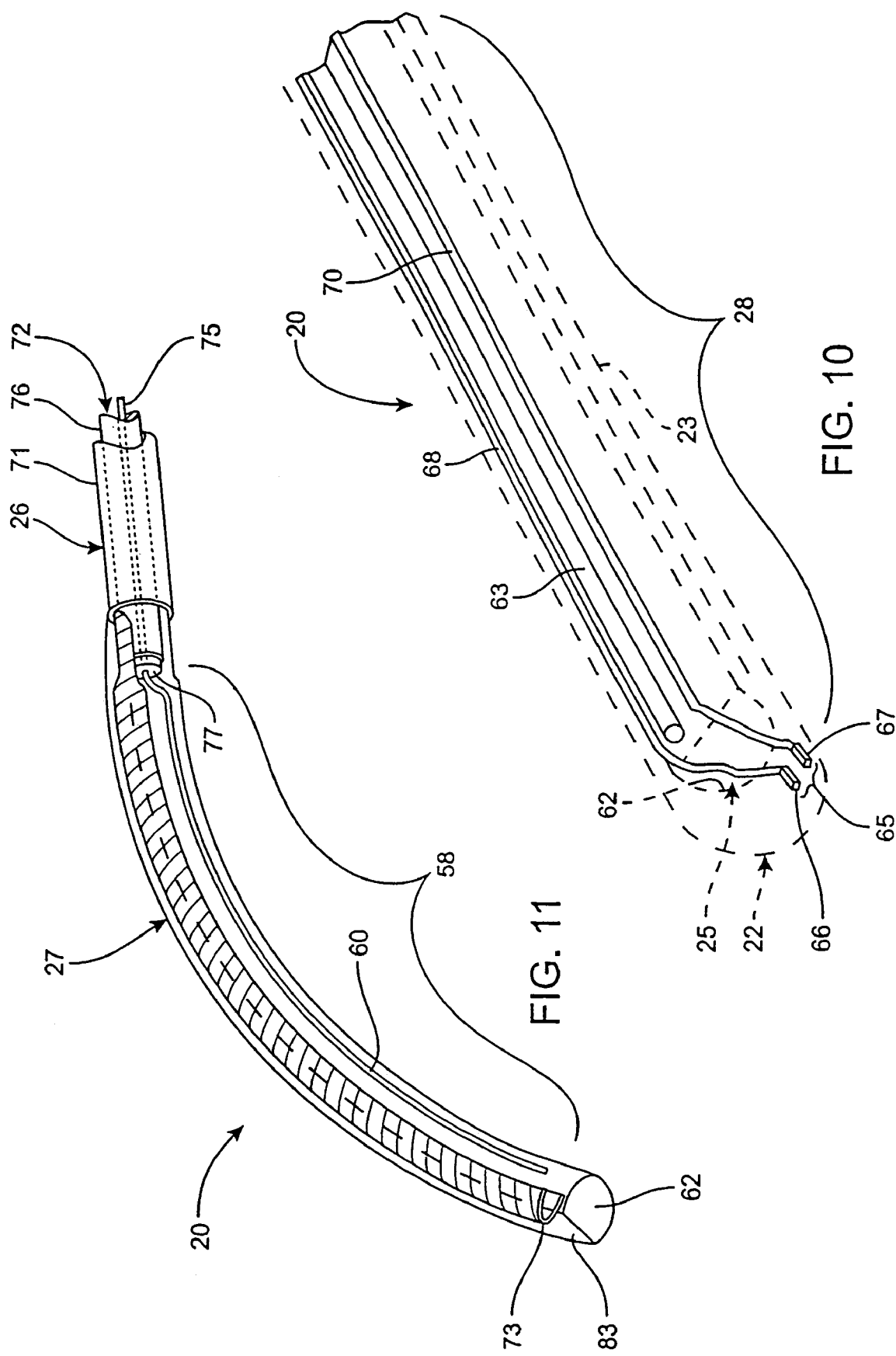

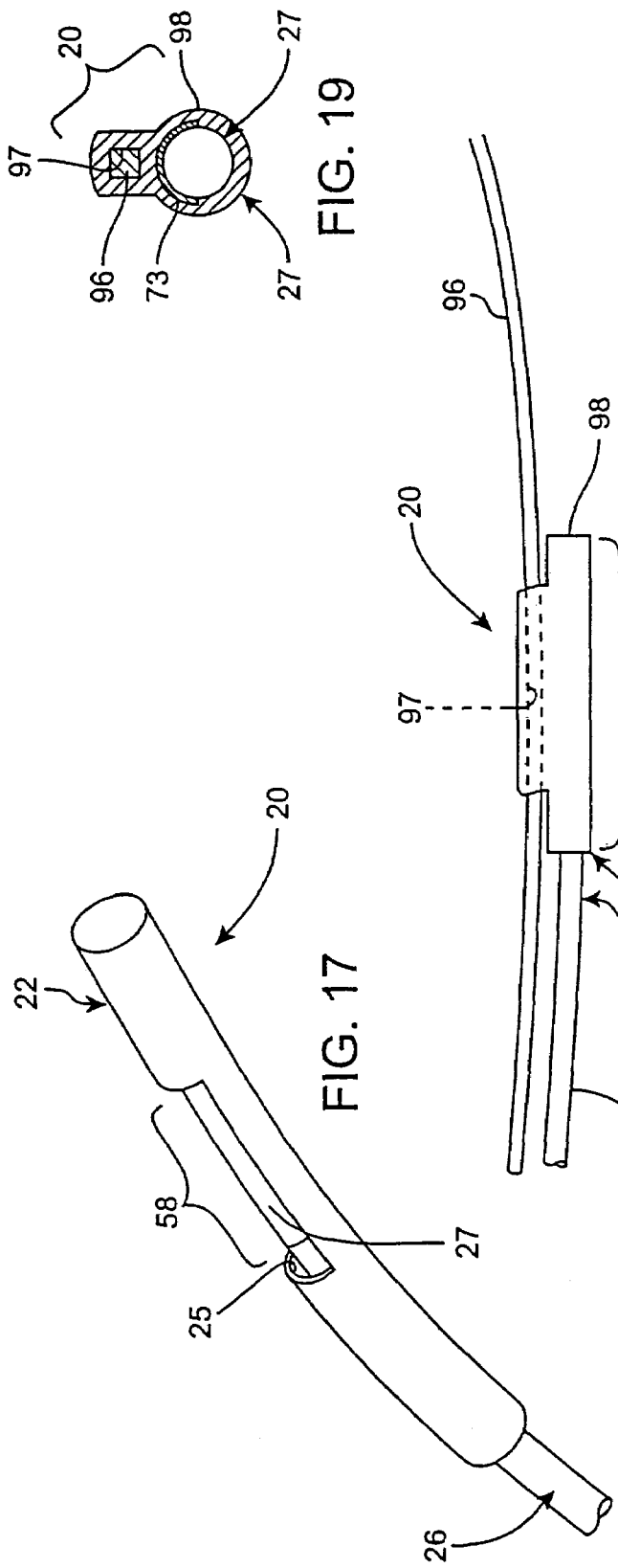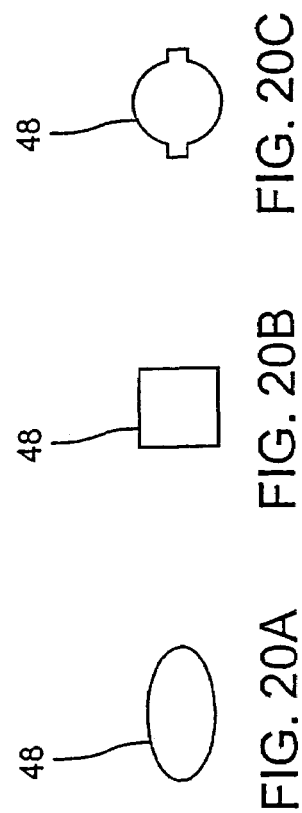

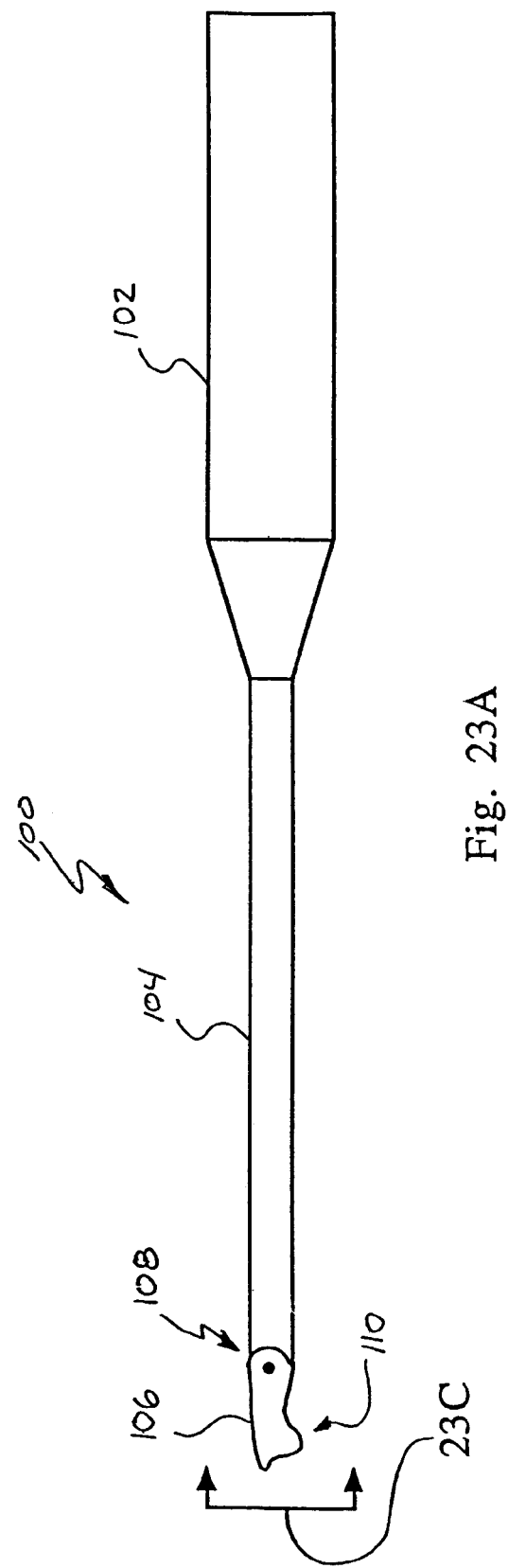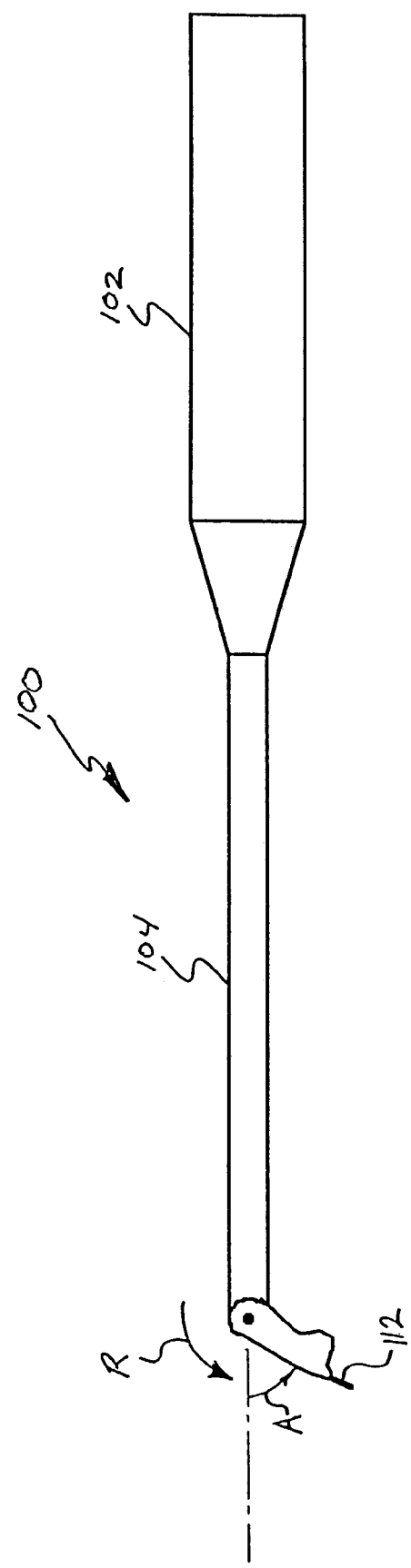
Fig. 23A
Fig. 23B

METHOD OF POSITIONING A MEDICAL INSTRUMENT

This application is a continuation of U.S. patent application Ser. No. 09/872,652, filed on Jun. 1, 2001, now issued as U.S. Pat. No. 6,802,840, which is a continuation-in-part of U.S. patent application Ser. No. 09/751,472, filed Dec. 29, 2000, the subject matters of which are incorporated herein in the entireties by this reference.

BACKGROUND OF THE INVENTION

1. Field of Invention

The present invention relates, generally, to ablation instrument systems that use ablative energy to ablate internal bodily tissues. More particularly, to preformed guide apparatus which cooperate with energy delivery arrangements to direct the ablative energy in selected directions along the guide apparatus.

2. Description of the Prior Art

It is well documented that atrial fibrillation, either alone or as a consequence of other cardiac disease, continues to persist as the most common cardiac arrhythmia. According to recent estimates, more than two million people in the U.S. suffer from this common arrhythmia, roughly 0.15% to 1.0% of the population. Moreover, the prevalence of this cardiac disease increases with age, affecting nearly 8% to 17% of those over 60 years of age.

Atrial arrhythmia may be treated using several methods. Pharmacological treatment of atrial fibrillation, for example, is initially the preferred approach, first to maintain normal sinus rhythm, or secondly to decrease the ventricular response rate. Other forms of treatment include drug therapies, electrical cardioversion, and RF catheter ablation of selected areas determined by mapping. In the more recent past, other surgical procedures have been developed for atrial fibrillation, including left atrial isolation, transvenous catheter or cryosurgical ablation of His bundle, and the Corridor procedure, which have effectively eliminated irregular ventricular rhythm. However, these procedures have for the most part failed to restore normal cardiac hemodynamics, or alleviate the patient's vulnerability to thromboembolism because the atria are allowed to continue to fibrillate. Accordingly, a more effective surgical treatment was required to cure medically refractory atrial fibrillation of the Heart.

On the basis of electrophysiologic mapping of the atria and identification of macroreentrant circuits, a surgical approach was developed which effectively creates an electrical maze in the atrium (i.e., the MAZE procedure) and precludes the ability of the atria to fibrillate. Briefly, in the procedure commonly referred to as the MAZE III procedure, strategic atrial incisions are performed to prevent atrial reentry circuits and allow sinus impulses to activate the entire atrial myocardium, thereby preserving atrial transport function postoperatively. Since atrial fibrillation is characterized by the presence of multiple macroreentrant circuits that are fleeting in nature and can occur anywhere in the atria, it is prudent to interrupt all of the potential pathways for atrial macroreentrant circuits. These circuits, incidentally, have been identified by intraoperative mapping both experimentally and clinically in patients.

Generally, this procedure includes the excision of both atrial appendages, and the electrical isolation of the pulmonary veins. Further, strategically placed atrial incisions not only interrupt the conduction routes of the common reentrant circuits, but they also direct the sinus impulse from the sinoatrial node to the atrioventricular node along a specified route. In essence, the entire atrial myocardium, with the exception of the atrial appendages and the pulmonary veins, is electrically activated by providing for multiple blind alleys off the main conduction route between the sinoatrial node to the atrioventricular node. Atrial transport function is thus preserved postoperatively as generally set forth in the series of articles: Cox, Schuessler, Boineau, Canavan, Cain, Lindsay, Stone, Smith, Corr, Change, and D'Agostino, Jr., *The Surgical Treatment Atrial Fibrillation* (pts. 1-4), 101 THORAC CARDIOVASC SURG., 402-426, 569-592 (1991).✓

While this MAZE III procedure has proven effective in ablating medically refractory atrial fibrillation and associated detrimental sequelae, this operational procedure is traumatic to the patient since this is an open-heart procedure and substantial incisions are introduced into the interior chambers of the Heart. Consequently, other techniques have been developed to interrupt atrial fibrillation restore sinus rhythm. One such technique is strategic ablation of the atrial tissues through ablation catheters.

Most approved ablation catheter systems now utilize radio frequency (RF) energy as the ablating energy source. Accordingly, a variety of RF based catheters and power supplies are currently available to electrophysiologists. However, radio frequency energy has several limitations including the rapid dissipation of energy in surface tissues resulting in shallow "burns" and failure to access deeper arrhythmic tissues. Another limitation of RF ablation catheters is the risk of clot formation on the energy emitting electrodes. Such clots have an associated danger of causing potentially lethal strokes in the event that a clot is dislodged from the catheter. It is also very difficult to create continuous long lesions with RF ablation instruments.

As such, catheters which utilize other energy sources as the ablation energy source, for example in the microwave frequency range, are currently being developed. Microwave frequency energy, for example, has long been recognized as an effective energy source for heating biological tissues and has seen use in such hyperthermia applications as cancer treatment and preheating of blood prior to infusions. Accordingly, in view of the drawbacks of the traditional catheter ablation techniques, there has recently been a great deal of interest in using microwave energy as an ablation energy source. The advantage of microwave energy is that it is much easier to control and safer than direct current applications and it is capable of generating substantially larger and longer lesions than RF catheters, which greatly simplifies the actual ablation procedures. Such microwave ablation systems are described in the U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stern, et al, each of which is incorporated herein by reference.

Most of the existing microwave ablation catheters contemplate the use of longitudinally extending helical antenna coils that direct the electromagnetic energy in all radial directions that are generally perpendicular to the longitudinal axis of the catheter. Although such catheter designs work well for a number of applications, such radial output is inappropriate when the energy needs to be directed toward the tissue to ablate only.

Consequently, microwave ablation instruments have recently been developed which incorporate microwave antennas having directional reflectors. Typically, a tapered directional reflector is positioned peripherally around the microwave antenna to direct the waves toward and out of a window portion of the antenna assembly. These ablation instruments, thus, are capable of effectively transmitting electromagnetic energy in a more specific direction. For example, the electromagnetic energy may be transmitted generally perpendicular to the longitudinal axis of the catheter but constrained to a selected radial region of the antenna, or directly out the distal end of the instrument. Typical of these designs are described in the U.S. patent application Ser. Nos. 09/178,066, filed Oct. 23, 1998; and 09/333,747, filed Jun. 14, 1999, each of which is incorporated herein by reference.

In these designs, the resonance frequency of the microwave antenna is preferably tuned assuming contact between the targeted tissue or blood and a contact region of the antenna assembly extending longitudinally adjacent to the antenna longitudinal axis. Hence, should a portion of, or substantially all of, the exposed contact region of the antenna not be in contact with the targeted tissue or blood during ablation, the resonance frequency will be adversely changed and the antenna will be untuned. As a result, the portion of the antenna not in contact with the targeted tissue or blood will radiate the electromagnetic radiation into the surrounding air. The efficiency of the energy delivery into the tissue will consequently decrease which in turn causes the penetration depth of the lesion to decrease.

This is particularly problematic when the microwave antenna is not in the blood pool, or when the tissue surfaces are substantially curvilinear, or when the targeted tissue for ablation is difficult to access, such as in the interior chambers of the Heart. Since these antenna designs are generally relatively rigid, it is often difficult to maneuver substantially all of the exposed contact region of the antenna into abutting contact against the targeted tissue. In these instances, several ablation instruments, having antennas of varying length and shape, may be necessary to complete just one series of ablations.

SUMMARY OF THE INVENTION

Accordingly, a system for ablating a selected portion of a contact surface of biological tissue is provided. The system is particularly suitable to ablate cardiac tissue, and includes an elongated ablation sheath having a preformed shape adapted to substantially conform a predetermined surface thereof with the contact surface of the tissue. The ablation sheath defines an ablation lumen extending therethrough along an ablation path proximate to the predetermined surface. An elongated ablative device includes a flexible ablation element which cooperate with an ablative energy source which is sufficiently strong for tissue ablation. The ablative device is formed and dimensioned for longitudinal sliding receipt through the ablation lumen of the ablation sheath for selective placement of the ablative device along the ablation path created by the ablation sheath. The ablation lumen and the ablative device cooperate to position the ablative device proximate to the ablation sheath predetermined surface for selective ablation of the selected portion.

Accordingly, the ablation sheath in its preshaped form functions as a guide device to guide the ablative device along the ablation path when the predetermined surface of the ablation sheath properly contacts the biological tissue. Further, the cooperation between the ablative device and the ablation lumen, as the ablative device is advanced through the lumen, positions the ablative device in a proper orientation to facilitate ablation of the targeted tissue during the advancement. Thus, once the ablation sheath is stationed relative the targeted contact surface, the ablative device can be easily advanced along the ablation path to generate the desired tissue ablations.

In one embodiment, the ablative device is a microwave antenna assembly which includes a flexible shield device coupled to the antenna substantially shield a surrounding area of the antenna from the electromagnetic field radially generated therefrom while permitting a majority of the field to be directed generally in a predetermined direction toward the ablation sheath predetermined surface. The microwave antenna assembly further includes a flexible insulator disposed between the shield device and the antenna. A window portion of the insulator is defined which enables transmission of the directed electromagnetic field in the predetermined direction toward the ablation sheath predetermined surface. The antenna, the shield device and the insulator are formed for manipulative bending thereof, as a unit, to one of a plurality of contact positions to generally conform the window portion to the ablation sheath predetermined surface as the insulator and antenna are advanced through the ablation lumen.

In another embodiment, to facilitate alignment of the ablative device assembly in the ablation lumen, the ablative device provides a key device which is slidably received in a mating slot portion of the ablation lumen. In still another embodiment, the system includes a guide sheath defining a guide lumen formed and dimensioned for sliding receipt of the ablation sheath therethrough. The guide sheath is preshaped to facilitate positioning of the ablation sheath toward the selected portion of the contact surface when the ablation sheath is advanced through guide lumen.

The ablation sheath includes a bendable shape retaining member extending longitudinally therethrough which is adapted to retain the preformed shape of the ablation sheath once positioned out of the guide lumen of the guide sheath.

The ablative energy is preferably provided by a microwave ablative device. Other suitable tissue ablation devices, however, include cryogenic, ultrasonic, laser and radiofrequency, to name a few;

In another aspect of the present invention, a method for treatment of a Heart includes forming a penetration through a muscular wall of the Heart into an interior chamber thereof; and positioning a distal end of an elongated ablation sheath through the penetration. The ablation sheath defines an ablation lumen extending along an ablation path therethrough. The method further includes contacting, or bringing close enough, a predetermined surface of the elongated ablation sheath with a first selected portion of an interior surface of the muscular wall; and passing a flexible ablative device through the ablation lumen of the ablation sheath for selective placement of the ablative device along the ablation path. Once these events have been performed, the method includes applying the ablative energy, using the ablative device and the ablation energy source, which is sufficiently strong to cause tissue ablation.

In one embodiment, the passing is performed by incrementally advancing the ablative device along a plurality of positions of the ablation path to produce a substantially continuous lesion. Before the positioning event, the method includes placing a distal end of a guide sheath through the penetration, and then positioning the distal end of the ablation sheath through the guide lumen of the guide sheath.

In still another embodiment, before the placing event, piercing the muscular wall with a piercing sheath. The piercing sheath defines a positioning passage extending therethrough, The placing the distal end of a guide sheath is performed by placing the guide sheath distal end through the positioning passage of the piercing sheath.

In yet another configuration, the positioning the distal end event includes advancing the ablation sheath toward the first selected portion of the interior surface of the muscular wall through a manipulation device extending through a second penetration into the Heart interior chamber independent from the first named penetration.

In another embodiment, a system for ablating tissue within a body of a patient is provided including an elongated rail device and an ablative device. The radial device is adapted to be positioned proximate and adjacent to a selected tissue region to be ablated within the body of the patient. The ablative device includes a receiving passage configured to slideably receive the rail device longitudinally therethrough. This enables the ablative device to be slideably positioned along the rail substantially adjacent to or in contact with the selected tissue region. The ablative device, having an energy delivery portion which is adapted to be coupled to an ablative energy source, can then be operated to ablate the selected tissue region.

In this configuration, the ablative device is adapted to directionally emit the ablative energy from the energy delivery portion. A key assembly cooperates between the ablative device and the rail member, thus, to properly align the directionally emitted ablative energy toward the tissue region to be ablated. This primarily performed by providing a rail device with a non-circular transverse cross-sectional dimension. The receiving passage of the ablative device further includes a substantially similarly shaped non-circular transverse cross-section dimension to enable sliding of the ablative device in a manner continuously aligning the directionally emitted ablative energy toward the tissue region to be ablated as the ablative device advances along the rail device.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIGS. 2A-2D is series of fragmentary, side elevation views, in partial cross-section, of the Heart, and illustrating advancement of the ablation system of present invention into the left atrium for ablation of the targeted tissue.

FIG. 10 is an enlarged, front elevation view, in cross-section, of the antenna assembly taken substantially along the plane of the line 10-10 in FIG. 9.

FIG. 11 is a diagrammatic top plan view of an alternative embodiment microwave ablation instrument system constructed in accordance with one embodiment of the present invention.

FIG. 17 is an enlarged, fragmentary, top perspective view of an alternative embodiment ablation sheath having an opened window portion.

FIG. 18 is a fragmentary, side elevation view of an alternative embodiment ablation assembly employing a rail system.

FIG. 19 is a front elevation view of the energy delivery portion of the ablation rail system taken along the plane of the line 19-19 in FIG. 18.

FIGS. 20A-20C are cross-sectional views of alternative key systems in accordance with the present invention.

FIGS. 23A-B are side elevation views of a positioning tool used in accordance with the present invention.

DETAILED DESCRIPTION OF THE INVENTION

Figure 1A:
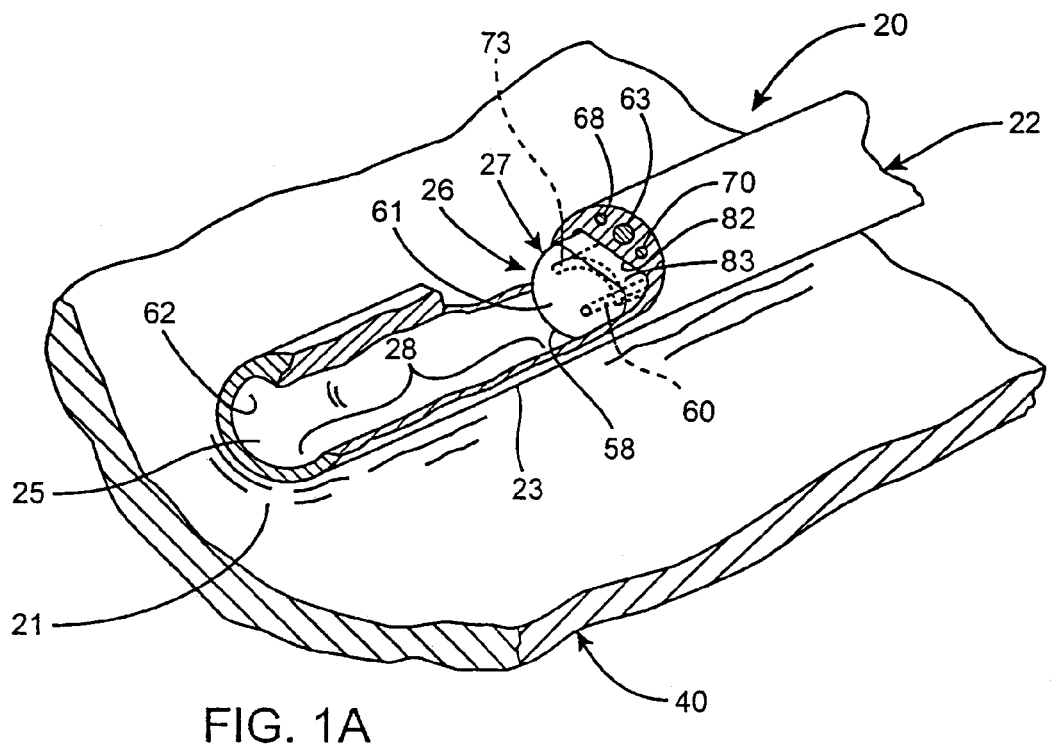
FIGS. 1A and 1B are fragmentary, top perspective views, partially broken-away, of the ablation system constructed in accordance with the present invention, and illustrating advancement of a bendable directional reflective microwave antenna assembly through an ablation lumen of a ablation sheath.
Figure 1B:
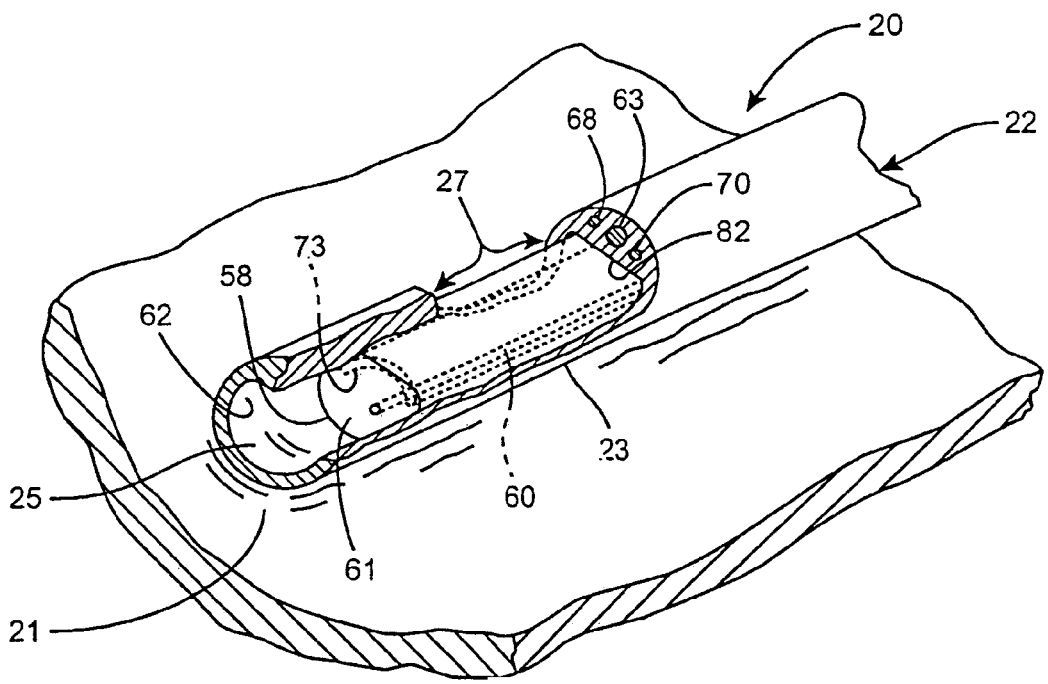

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various Figures.

Figure 6:
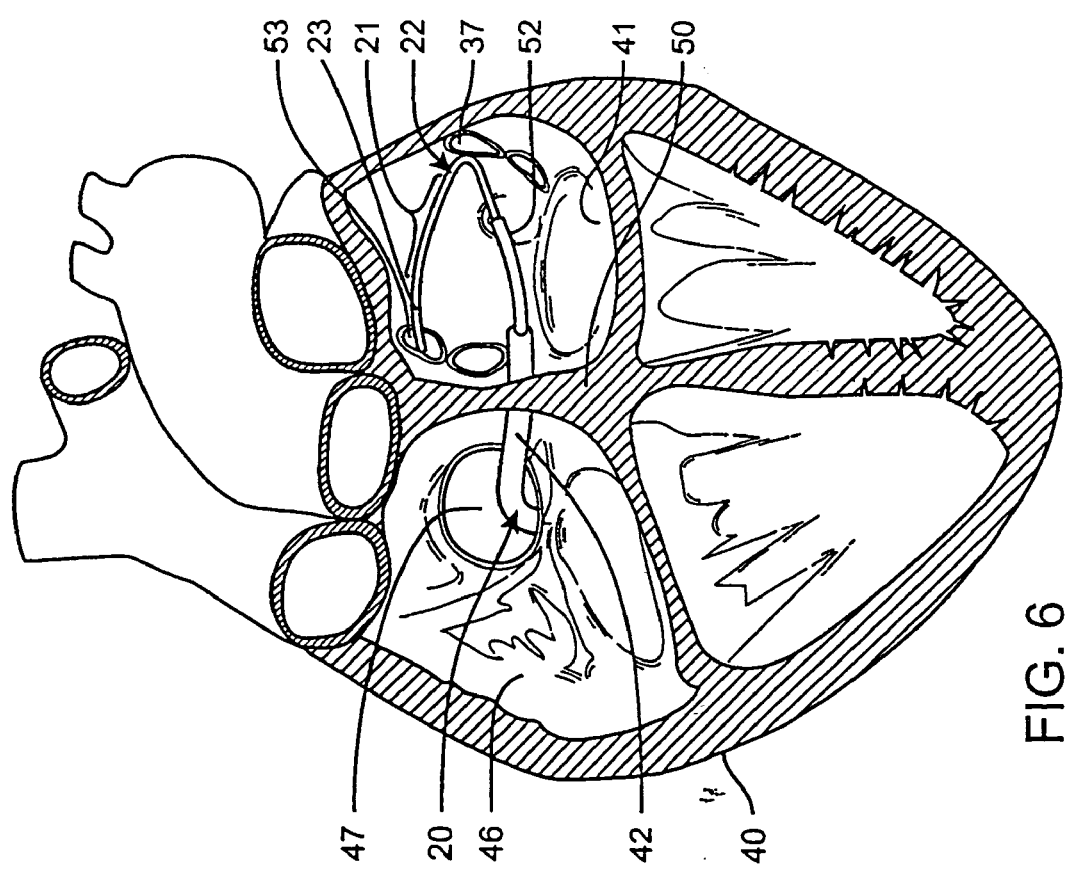
FIG. 6 is a fragmentary, side elevation view, in partial cross-section, of another embodiment of the ablation sheath of the present invention employed for lesion formation.

Turning generally now to FIGS. 1A-2D, an ablation system, generally designated 20, is provided for transmurally ablating a targeted tissue 21 of biological tissue. The system 20 is particularly suitable to ablate the epicardial or endocardial tissue 40 of the heart, and more particularly, to treat medically refractory atrial fibrillation of the Heart. The ablation system 20 for ablating tissue within a body of a patient includes an elongated flexible tubular member 22 having at least one lumen 25 (FIGS. 1A, 1B, 8 and 9) and including a pre-shaped distal end portion (E.g., FIGS. 2C, 6 and 7) which is shaped to be positioned adjacent to or in contact with a selected tissue region 21 within the body of the patient. An ablative device, generally designated 26, is configured to be slidably received longitudinally within the at least one lumen 25, and includes an energy delivery portion 27 located near a distal end portion of the ablative device 26 which is adapted to be coupled to an ablative energy source (not shown).

The ablative device is preferably provided by a microwave ablation device 26 formed to emit microwave energy sufficient to cause tissue ablation. As will be described in greater detail below, however, the ablative device energy may be provided by a laser ablation device, a Radio Frequency (RF) ablation device, an ultrasound ablation device or a cryoablation device.

The tubular member 22 is in the form of an elongated ablation sheath having, in a preferred embodiment, a resiliently preformed shape adapted to substantially conform a predetermined contact surface 23 of the sheath with the targeted tissue region 21. In another embodiment, the ablation sheath is malleable. Yet, in another embodiment, the ablation sheath is flexible. The lumen 25 of the tubular member extends therethrough along an ablation path proximate to the predetermined contact surface. Preferably, as will be described in more detail below, the ablative device 26 includes a flexible energy delivery portion 27 selectively generating an electromagnetic field which is sufficiently strong for tissue ablation. The energy delivery portion 27 is formed and dimensioned for longitudinal sliding receipt through the ablation lumen 25 of the ablation sheath 22 for selective placement of the energy delivery portion along the ablation path. The ablation lumen 25 and the ablative device 26 cooperate to position the energy delivery portion 27 proximate to the ablation sheath 22 predetermined contact surface 23 of the sheath for selective transmural ablation of the targeted tissue 21 within the electromagnetic field when the contact surface 23 strategically contacts or is positioned close enough to the targeted tissue 21.

Accordingly, in one preferred embodiment, the pre-shaped ablation sheath 22 functions to unidirectionally guide or position the energy delivery portion 27 of the ablative device 26 properly along the predetermined ablation path 28 proximate to the targeted tissue region 21 as the energy delivery portion 27 is advanced through the ablation lumen 25. By positioning the energy delivery portion 27, which is preferably adapted to emit a directional ablation field, at one of a plurality of positions incrementally along the ablation path (FIGS. 1A and 1B) in the lumen 25, a single continuous or plurality of spaced-apart lesions can be formed. In other instances, the antenna length may be sufficient to extend along the entire ablation path 28 so that only a single ablation sequence is necessary.

Figure 3:
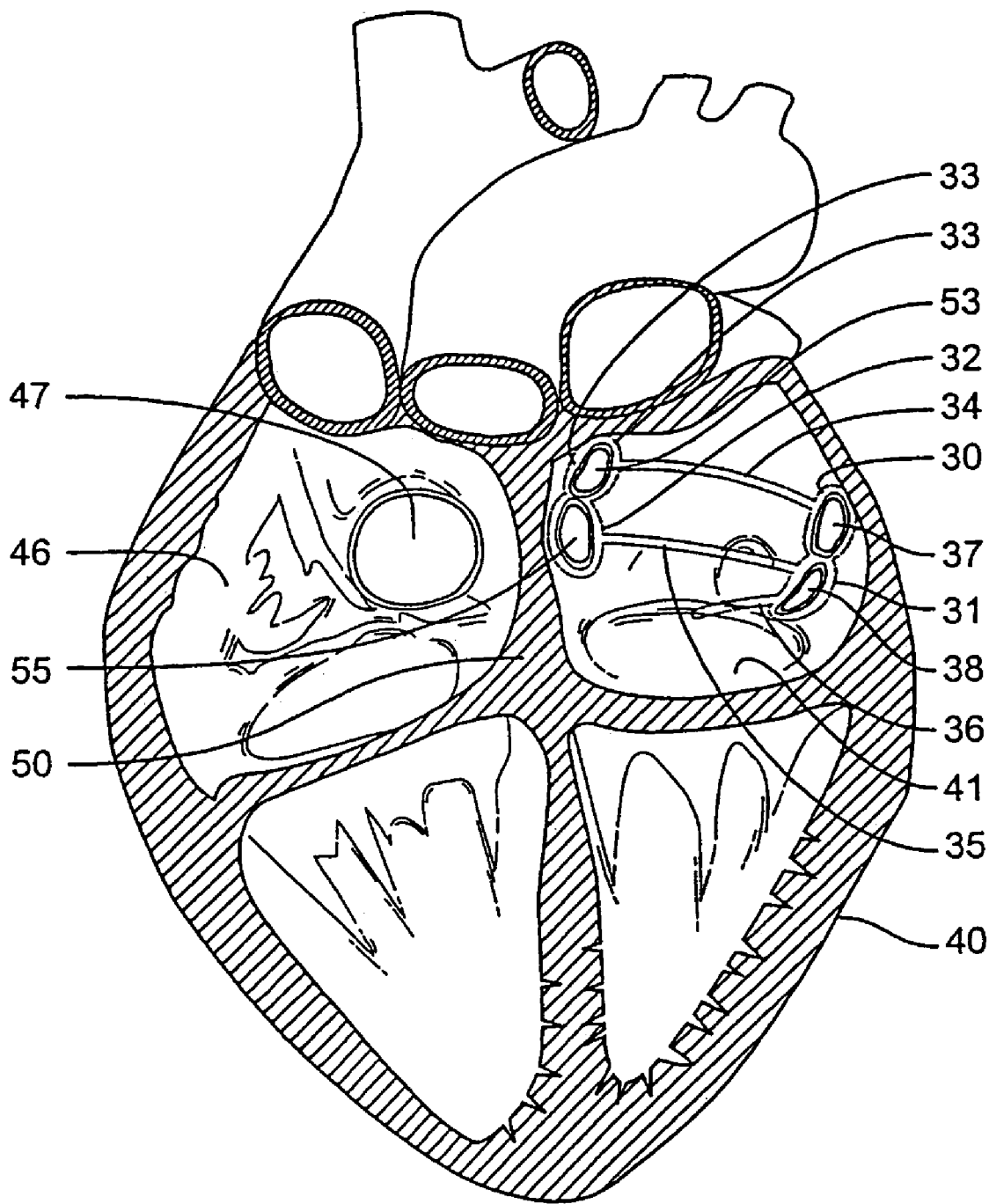
FIG. 3 is a fragmentary, side elevation view, in partial cross-section, of the Heart showing a pattern of ablation lesions to treat atrial fibrillation.

While the method and apparatus of the present invention are applicable to ablate any biological tissue which requires the formation of controlled lesions (as will be described in greater detail below), this ablation system is particularly suitable for ablating endocardial or epicardial tissue of the Heart. For example, the present invention may be applied in an intra-coronary configuration where the ablation procedure is performed on the endocardium of any cardiac chamber. Specifically, such ablations may be performed on the isthmus to address atrial flutter, or around the pulmonary vein ostium, electrically isolating the pulmonary veins, to treat medically refractory atrial fibrillation (FIG. 3). This procedure requires the precise formation of strategically placed endocardial lesions 30-36 which collectively isolate the targeted regions. By way of example, any of the pulmonary veins may be collectively isolated to treat chronic atrial fibrillation. The annular lesion isolating one or more than one pulmonary vein can be linked with another linear lesion joining the mitral valve annulus. In another example, the annular lesion isolating one or more than one pulmonary vein can be linked with another linear lesion joining the left atrium appendage.

Figure 12:
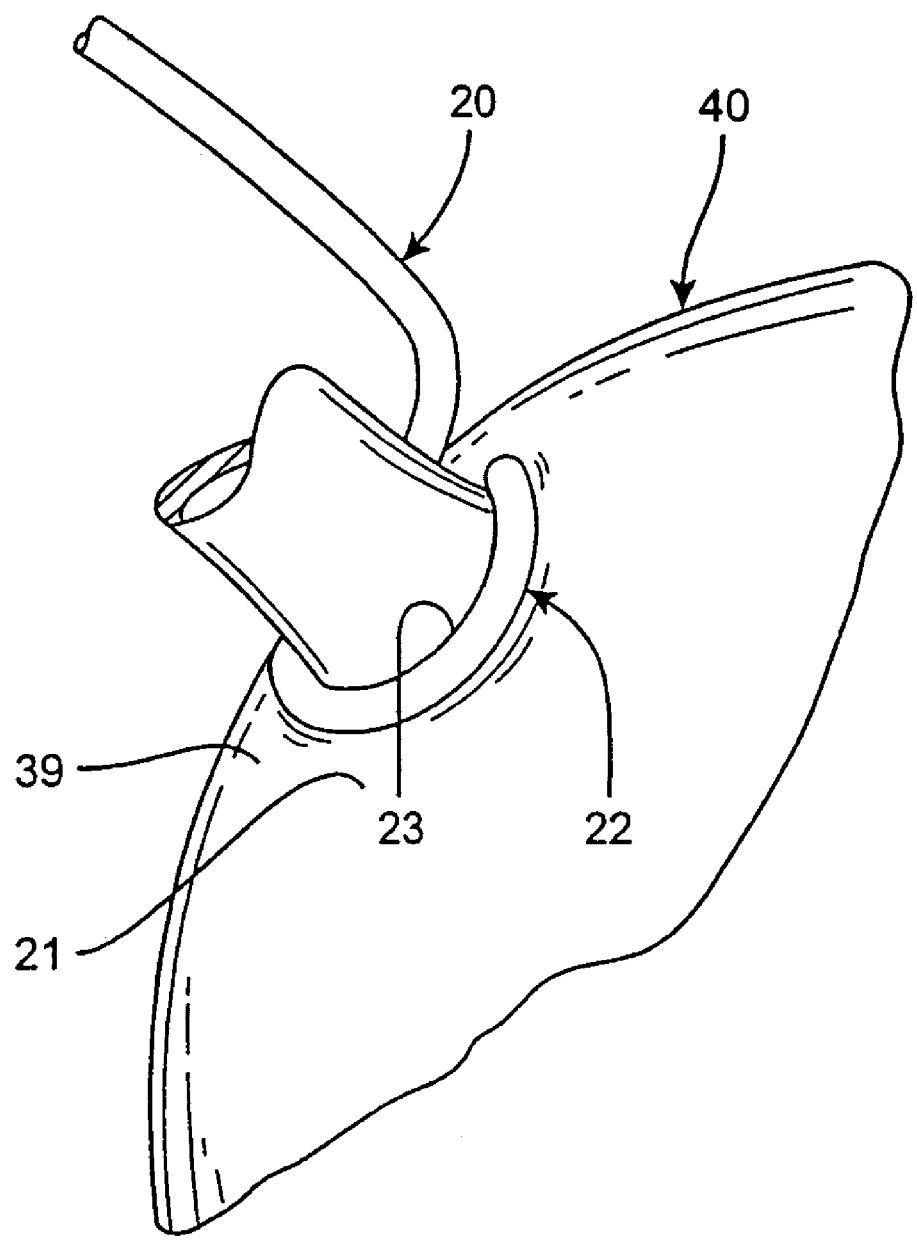
FIG. 12 is an enlarged, fragmentary, top perspective view of the ablation instrument system of FIG. 11 illustrated in a bent position to conform to a surface of the tissue to be ablated.
Figure 13A:
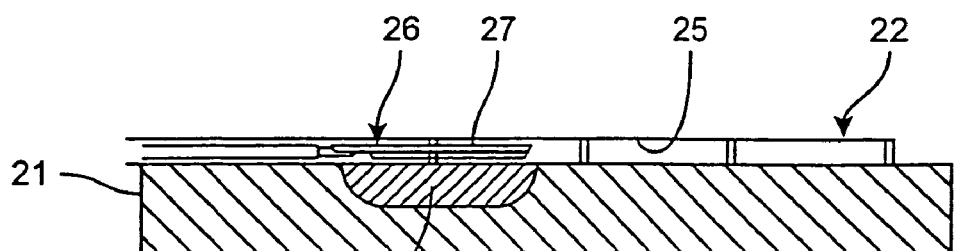
FIGS. 13A-13D is a series of side elevation views, in cross-section, of the ablation sheath of the present invention illustrating advancement of the ablation device incrementally through the ablation sheath to form plurality of overlapping lesions.
Figure 13B:
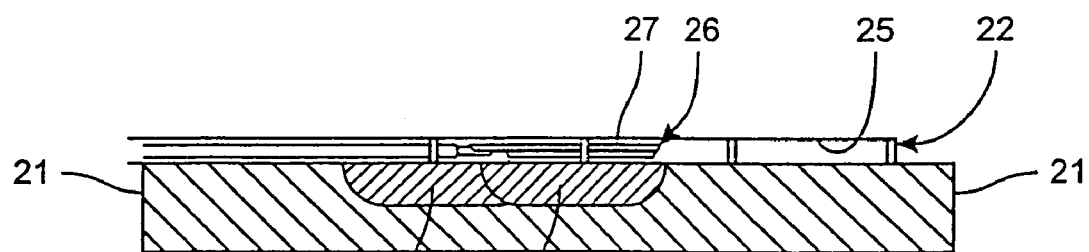
Figure 13C:
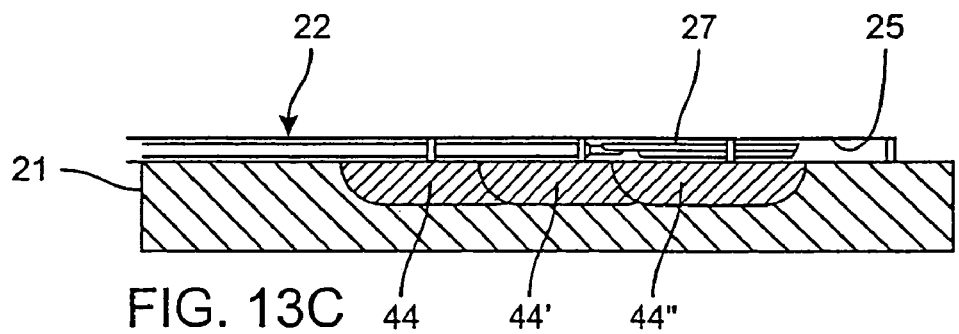
Figure 13D:
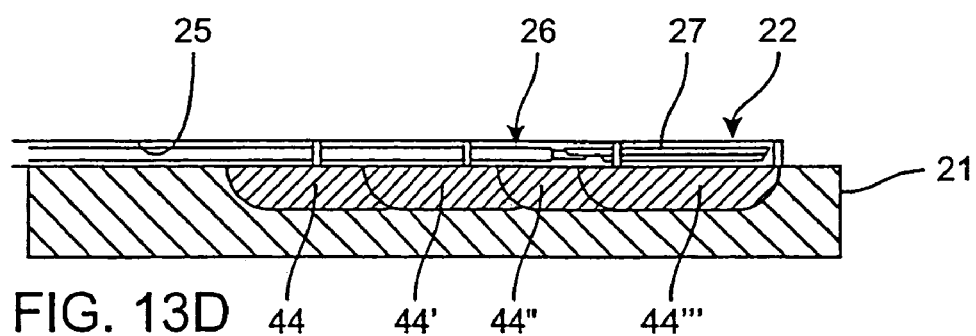

In a preferred embodiment, the pre-shaped ablation sheath 22 and the sliding ablative device 26 may applied to ablate the epicardial tissue 39 of the Heart 40 as well (FIG. 12). An annular ablation, for instance, may be formed around the pulmonary vein for electrical isolation from the left atrium. As another example, the lesions may be created along the transverse sinus and oblique sinus as part of the collective ablation pattern to treat atrial fibrillation for example.

The application of the present invention, moreover, is preferably performed through minimally invasive techniques. It will be appreciated, however, that the present invention may be applied through open chest techniques as well.

Briefly, to illustrate the operation of the present invention, a flexible pre-shaped tubular member (i.e., ablation sheath 22) in the form of a pigtail is shown in FIGS. 2C and 2*d* which is specifically configured to electrically isolate a pulmonary vein of the Heart 40. The isolating lesions are preferably made on the posterior wall of the left atrium, around the ostium of one, or more than one of a pulmonary vein.

Figure 4A:
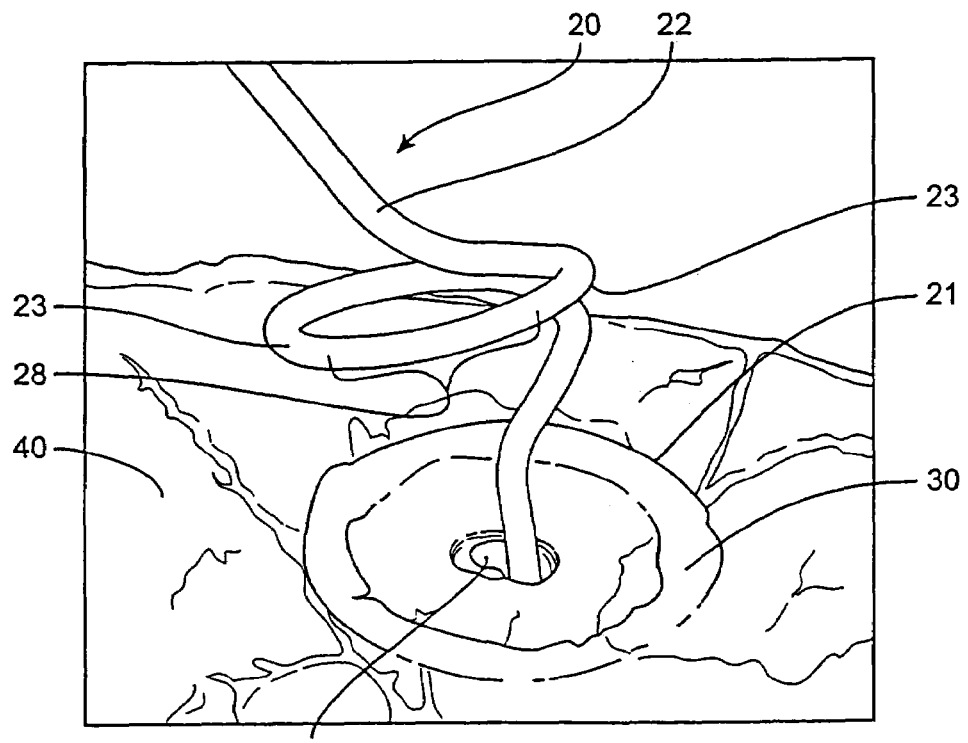
FIGS. 4A and 4B are a series of enlarged, fragmentary, top perspective view of a pigtail ablation sheath of the ablation system of FIGS. 2C and 2D, and exemplifying the ablation sheath being advanced into one of the pulmonary vein orifices.
Figure 4B:
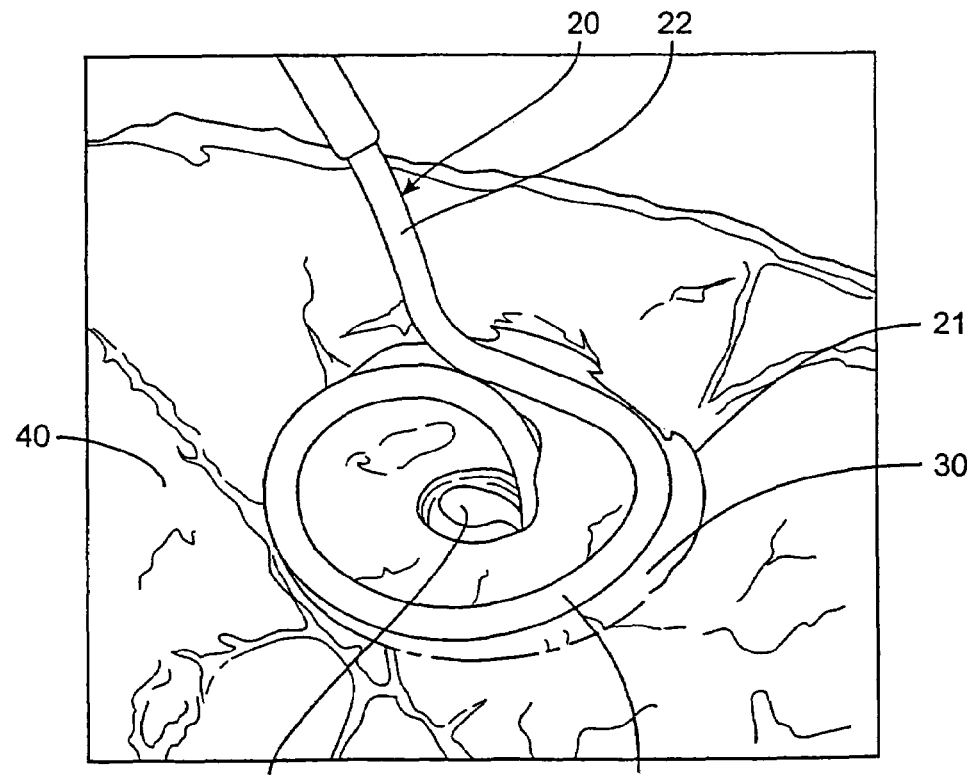

In this example and as illustrated in FIGS. 4A and 4B, a distal end of the pigtail-shaped ablation sheath or tubular member 22 is positioned into the left superior pulmonary vein orifice 37 from the left atrium 41. As the ablation sheath 22 is further advanced, a predetermined contact surface 23 of the ablation sheath is urged adjacent to or into contact with the endocardial surface of the targeted tissue region 21 (FIGS. 2D and 4B). Once the ablation sheath 22 is properly positioned and oriented, the ablative device 26 is advanced through the ablation lumen 25 of the ablation sheath 22 (FIGS. 1A and 1B) which moves the energy delivery portion 27 of the ablative device along the ablation path. When the energy delivery portion 27 is properly oriented and positioned in the ablation lumen 25, the directional ablation field may be generated to incrementally ablate (FIGS. 13A-13D) the epicardial surface of the targeted tissue 21 along the ablation path to isolate the Left Superior Pulmonary Vein (LIPV)

Accordingly, as shown in FIGS. 13A-13D, as the energy delivery portion 27 is incrementally advanced through the lumen 25, overlapping lesion sections 44-44''' are formed by the ablation field which is directional in one preferred embodiment. Collectively, a continuous lesion or series of lesions can be formed which essentially three-dimensionally "mirror" the shape of the contact surface 23 of the ablation sheath 22 which is positioned adjacent to or in contact with the targeted tissue region. These transmural lesions may thus be formed in any shape on the targeted tissue region such as rectilinear, curvilinear or circular in shape. Further, depending upon the desired ablation lines pattern, both opened and closed path formation can be constructed.

Figure 5:
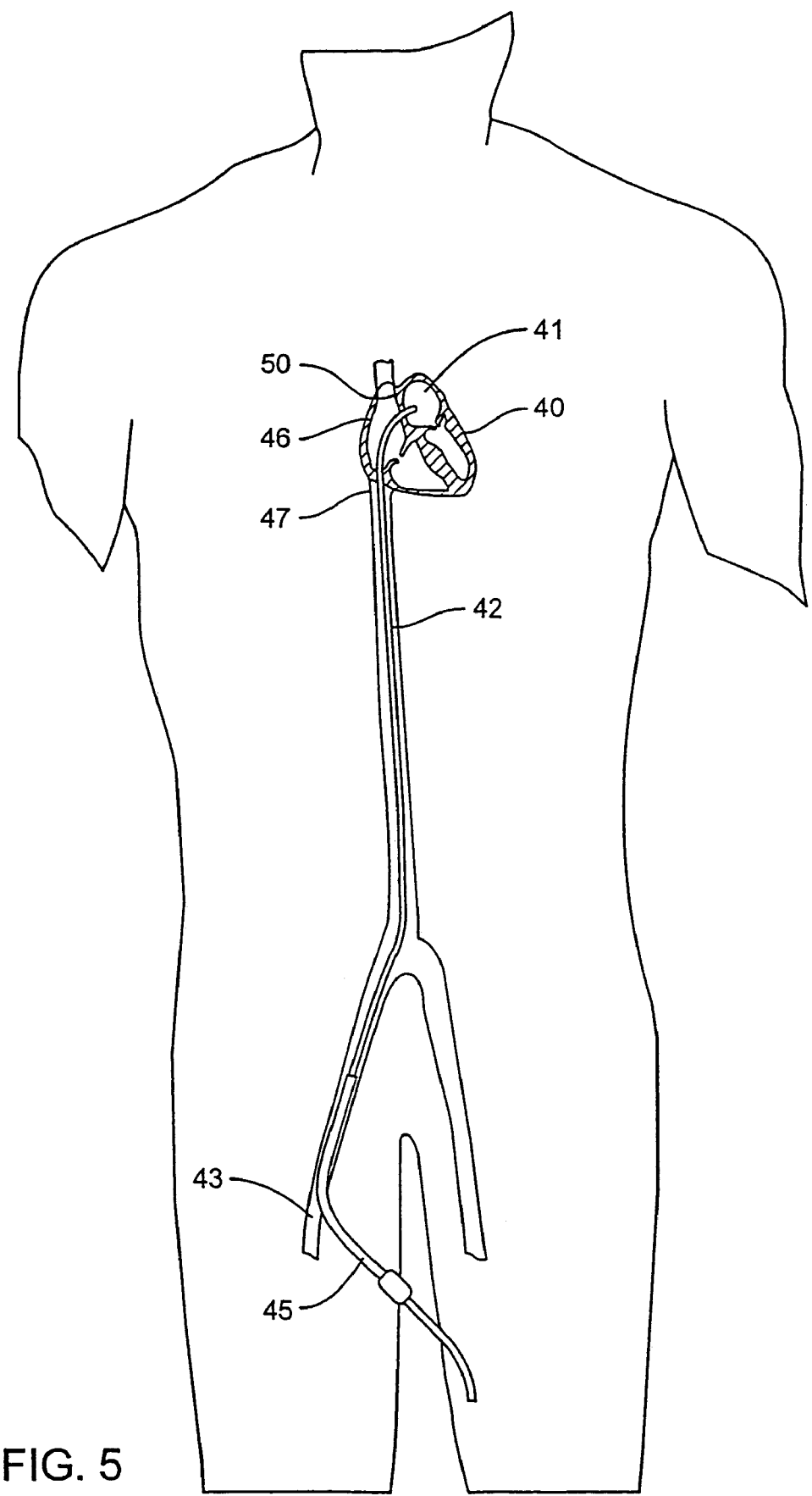
FIG. 5 is a front schematic view of a patient's cardiovascular system illustrating the positioning of a trans-septal piercing sheath through the septum wall of the patient's Heart.

Referring now to FIGS. 2A, 2D and 5, a minimal invasive application of the present invention is illustrated for use in ablating Heart tissue. By way of example, a conventional trans-septal piercing sheath 42 is introduced into the femoral vein 43 through a venous cannula 45 (FIG. 5). The piercing sheath is then intravenously advanced into the right atrium 46 of the Heart 40 through the inferior vena cava orifice 47. These piercing sheaths are generally resiliently pre-shaped to direct a conventional piercing device 48 toward the septum wall 50. The piercing device 48 and the piercing sheath 42 are manipulatively oriented and further advanced to pierce through the septum wall 50, as a unit, of access into the left atrium 41 of the Heart 40 (FIG. 2A).

These conventional devices are commonly employed in the industry for accessing the left atrium or ventricle, and have an outer diameter in the range of about 0.16 inch to about 0.175 inch, while having an inner diameter in the range of about 0.09 inch to about 0.135 inch.

Once the piercing device 48 is withdrawn from a positioning passage 51 (FIG. 8) of the piercing sheath 42, a guide sheath 52 of the ablation system 20 is slidably advanced through the positioning passage and into a cardiac chamber such as the left atrium 41 thereof (FIG. 2B). The guide sheath 52 is essentially a pre-shaped, open-ended tubular member which is inserted into the coronary circulation to direct and guide the advancing ablation sheath 22 into a selected cardiac chamber (i.e., the left atrium, right atrium, left ventricle or right ventricle) and toward the general direction of the targeted tissue. Thus, the guide sheath 52 and the ablation sheath 22 telescopically cooperate to position the predetermined contact surface 23 thereof substantially adjacent to or in contact with the targeted tissue region.

Moreover, the guide sheath and the ablation sheath cooperate to increase the structural stability of the system as the ablation sheath is rotated and manipulated from its proximal end into ablative contact with the targeted tissue 21 (FIG. 2A). As the distal curved portions of the ablation sheath 22, which is inherently longer than the guide sheath, is advanced past the distal lumen opening of the guide sheath, these resilient curved portions will retain their original unrestrained shape.

The telescopic effect of these two sheaths is used to position the contact surface 23 of the ablation sheath 22 substantially adjacent to or in contact with the targeted tissue. Thus, depending upon the desired lesion formation, the same guide sheath 52 may be employed for several different procedures. For example, the lesion 30 encircling the left superior pulmonary vein ostium and the Left Inferior Pulmonary Vein Ostium (RIPVO) lesion 31 (FIG. 3) may be formed through the cooperation of the pigtail ablation sheath 22 and the same guide sheath 52 of FIGS. 2B and 2D, while the same guide sheath may also be utilized with a different ablation sheath 22 (FIG. 4) to create the long linear lesion 34 as shown in FIG. 3.

Figure 7:
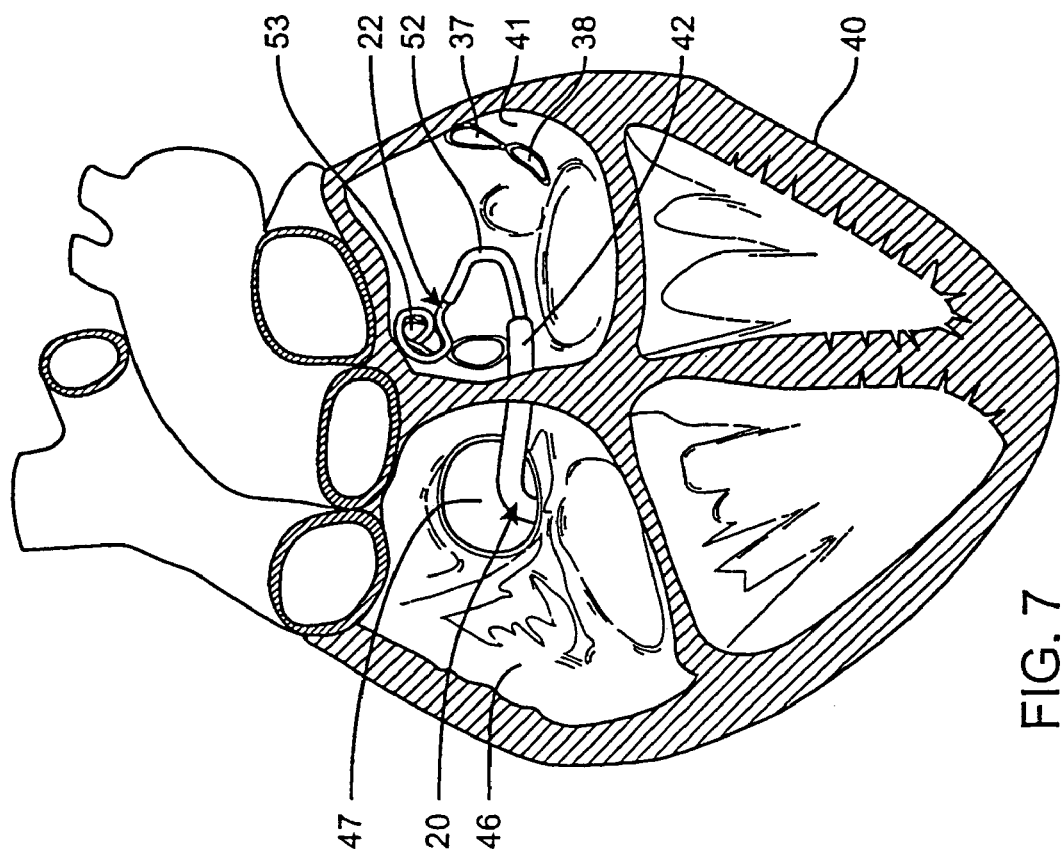
FIG. 7 is a fragmentary, side elevation view, in partial cross-section, of yet another embodiment of the ablation sheath of the present invention employed for another lesion formation.

In contrast, as illustrated in FIG. 7, another guide sheath 52 having a different pre-shaped distal end section may be applied to direct the advancing ablation sheath 22 back toward the in the left and right superior pulmonary vein orifices 53, 55. Thus, several pre-shaped guide sheaths, and the corresponding ablation sheaths, as will be described, cooperate to create a predetermined pattern of lesions (E.g., a MAZE procedure) on the tissue.

In the preferred embodiment, the guide sheath 52 is composed of a flexible material which resiliently retains its designated shape once external forces urged upon the sheath are removed. These external forces, for instance, are the restraining forces caused by the interior walls 56 of the trans-septal piercing sheath 42 as the guide sheath 52 is advanced or retracted therethrough. While the guide sheath 52 is flexible, it must be sufficiently rigid so as to substantially retain its original unrestrained shape, and not to be adversely influenced by the ablation sheath 22, as the ablation sheath is advanced through the lumen of the guide sheath. Such flexible, biocompatible materials may be composed of braided Pebax or the like having an outer diameter formed and dimensioned for sliding receipt longitudinally through the positioning passage 51 of the trans-septal piercing sheath 42. The outer dimension is therefore preferably cylindrical having an outer diameter in the range of about 0.09 inch to about 0.145 inch, and more preferably about 0.135", while having an inner diameter in the range of about 0.05 inch to about 0.125 inch, and more preferably about 0.115". This cylindrical dimension enables longitudinal sliding receipt, as well as axial rotation, in the positioning passage 51 to properly place and advance the guide sheath 52. Thus, the dimensional tolerance between the cylindrical-shaped, outer peripheral wall of the guide sheath 52 and the interior walls 56 of the trans-septal piercing sheath 42 should be sufficiently large to enable reciprocal movement and relative axial rotation therebetween, while being sufficiently small to substantially prevent lateral displacement therebetween as the ablation sheath 22 is urged into contact with the targeted tissue 21. For example, the dimensional tolerance between the transverse cross-sectional periphery of the interior walls 56 of the positioning passage 51 and that of the substantially conforming guide sheath 52 should be in the range of about 0.005 inches to about 0.020 inches.

To increase the structural integrity of the guide sheath 52, metallic braids 57 are preferably incorporated throughout the sheath when the guide sheath is molded to its preformed shape. These braids 57 are preferably provided by 0.002" wires composed of 304 stainless steel evenly spaced about the sheath.

Once the guide sheath 52 is properly positioned and oriented relative the trans-septal sheath 42, the ablation sheath 22 is advanced through a guide lumen 54 (FIG. 8) of the guide sheath 52 toward the targeted tissue. Similar to the pre-shaped guide sheath 52, the ablation sheath 22 is pre-shaped in the form of the desired lesions to be formed in the endocardial surface of the targeted tissue 21. As best viewed in FIGS. 2D, 6 and 7, each ablation sheath 52 is adapted facilitate an ablation in the targeted tissue 21 generally in the shape thereof. Thus, several pre-shaped ablation sheaths cooperate to form a type of steering system to position the ablation device about the targeted tissue. Collectively, a predetermined pattern of linear and curvilinear lesions (E.g., a MAZE procedure) can be ablated on the targeted tissue region.

Again, similar to the guide sheath 52, the ablation sheath 22 is composed of a flexible material which resiliently retains its designated shape once external forces urged upon the sheath are removed. These external forces, for instance, are the restraining forces caused by the interior walls 59 defining the guide lumen 54 of the guide sheath 52 as the ablation sheath 22 is advanced or retracted therethrough. Such flexible, biocompatible materials may be composed of Pebax or the like having an outer diameter formed and dimensioned for sliding receipt longitudinally through the guide lumen 54 of the ablation sheath 22. As mentioned, the inner diameter of the guide lumen 54 is preferably in the range of about 0.050 inch to about 0.125 inch, and more preferably about 0.115", while the ablation sheath 26 has an outer diameter in the range of about 0.40 inch to about 0.115 inch, and more preferably about 0.105".

The concentric cylindrical dimensions enable longitudinal sliding receipt, as well as axial rotation, of the ablation sheath 22 in the guide lumen 54 to properly place and advance the it toward the targeted tissue 21. Thus, the dimensional tolerance between the cylindrical-shaped, outer peripheral wall of the ablation sheath 22 and the interior walls 59 of the guide lumen 54 of the guide sheath 52 should be sufficiently large to enable reciprocal movement and relative axial rotation therebetween, while being sufficiently small to substantially prevent lateral displacement therebetween as the ablation sheath 22 is urged into contact with the targeted tissue 21. For example, the dimensional tolerance between the transverse cross-sectional periphery of the guide lumen 54 and that of the substantially conforming energy delivery portion 27 should be in the range of about 0.001 inches to about 0.005 inches.

As above-indicated, the pre-shaped ablation sheath 22 facilitates guidance of the ablative device 26 along the predetermined ablation path 28. This is primarily performed by advancing the energy delivery portion 27 of the ablative device 26 through the ablation lumen 25 of the ablation sheath 22 which is preferably off-set from the longitudinal axis 78 thereof. As best viewed in FIGS. 8 and 9, this off-set positions the energy delivery portion 27 relatively closer to the predetermined contact surface 23 of the ablation sheath 22, and hence the targeted tissue 21. Moreover, when using directional fields such as those emitted from their energy delivery portion 27, it is important to provide a mechanism for continuously aligning the directional field of the energy delivery portion 27 with the tissue 21 targeted for ablation. Thus, in this design, the directional field must be continuously aligned with the predetermined contact surface 23 of the ablation sheath 22 as the energy delivery portion 27 is advanced through the ablation lumen 25 since the ablation sheath contact surface 23 is designated to contact or be close enough to the targeted tissue.

If the directional field is not aligned correctly, for example, the energy may be transmitted into surrounding fluids and tissues designated for preservation rather than into the targeted tissue region. Therefore, in accordance with another aspect of the present invention, a key structure 48 (FIGS. 1, 8 and 9) cooperates between the ablative device 26 and the ablation lumen 25 to orient the directive energy delivery portion 27 of the ablative device continuously toward the targeted tissue region 21 as it is advanced through the lumen. This key structure 48, thus, only allows receipt of the energy delivery portion 27 in the lumen in one orientation. More particularly, the key structure 48 continuously aligns a window portion 58 of the energy delivery portion 27 substantially adjacent the predetermined contact surface 23 of the ablation sheath 22 during advancement. This window portion 58, as will be described below, enables the transmission of the directed ablative energy from the energy delivery portion 27, through the contact surface 23 of the ablation sheath 22 and into the targeted tissue region. Consequently, the directional ablative energy emitted from the energy delivery portion will always be aligned with the contact surface 23 of the ablation sheath 22, which is positioned adjacent to or in contact with the targeted tissue region 21, to maximize ablation efficiency. By comparison, the ablation sheath 22 is capable of relatively free rotational movement axially in the guide lumen 54 of the guide sheath 52 for maneuverability and positioning of the ablation sheath therein.

Figure 8:
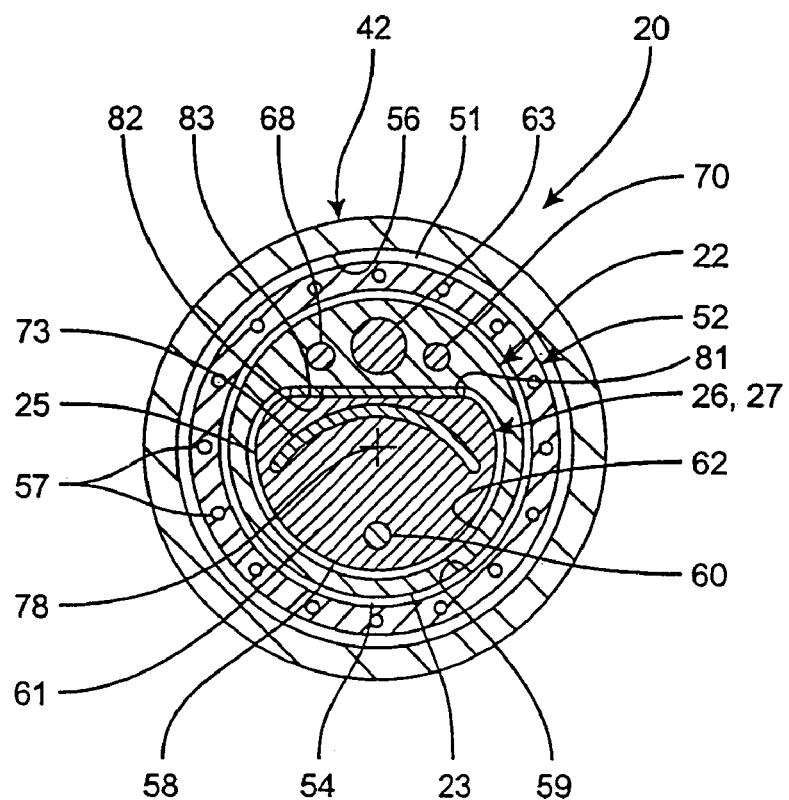
FIG. 8 is an enlarged, front elevation view, in cross-section, of the ablation system of FIG. 1 positioned through the trans-septal piercing sheath.
Figure 9:
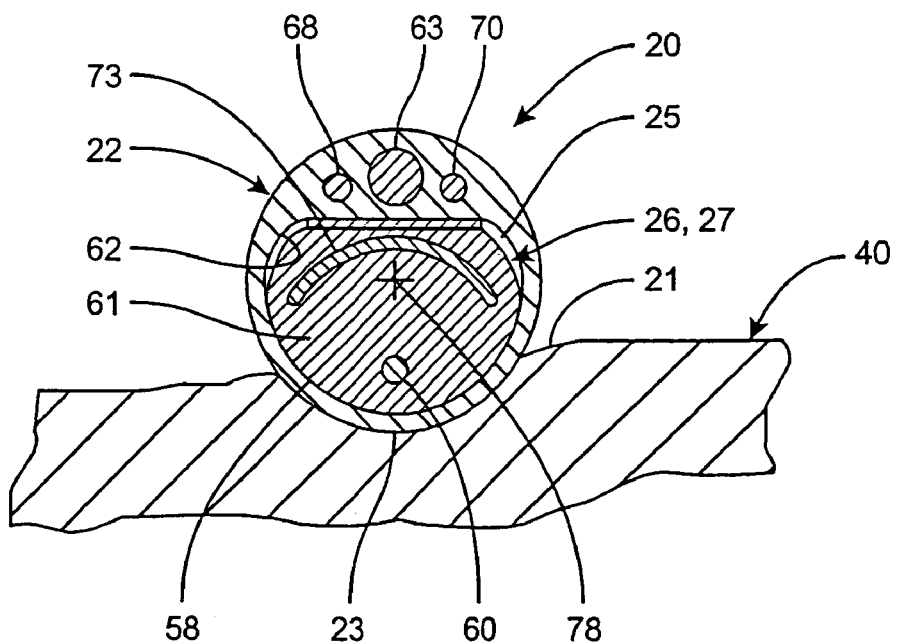
FIG. 9 is an enlarged, front elevation view, in cross-section, of the ablation sheath and the antenna assembly of the ablation system in FIG. 8 contacting the targeted tissue.

As mentioned, the transverse cross-sectional dimension of the energy delivery portion 27 is configured for sliding receipt in the ablation lumen 25 of the ablation sheath 22 in a manner positioning the directional ablative energy, emitted by the energy delivery portion, continuously toward the predetermined contact surface 23 of the ablation sheath 22. In one example, as shown in FIGS. 8 and 9, the transverse peripheral dimensions of the energy delivery portion 27 and the ablation lumen 25 are generally D-shaped, and substantially similar in dimension. Thus, the window portion 58 of the insulator 61, as will be discussed, is preferably semi-cylindrical and concentric with the interior wall 62 defining the ablation lumen 25 of the ablation sheath 22. It will be appreciated, however, that any geometric configuration may be applied to ensure unitary or aligned insertion. As another example, one of the energy delivery portion and the interior wall of the ablation lumen may include a key member and corresponding receiving groove, or the like. Such key and receiving groove designs, nonetheless, should avoid relatively sharp edges to enable smooth advancement and retraction of the energy delivery portion in the ablation lumen 25.

This dimension alignment relationship can be maintain along the length of the predetermined contact surface of the ablation sheath 22 as the energy delivery portion 27 is advanced through the ablation lumen whether in the configuration of FIGS. 2, 6, 7 or 12. In this manner, a physician may determine that once the predetermined contact surface 23 of the ablation sheath 22 is properly oriented and positioned adjacent or in contact against the targeted tissue 21, the directional component (as will be discussed) of the energy delivery portion 27 will then be automatically aligned with the targeted tissue as it is advanced through the ablation lumen 25. Upon selected ablation by the ablative energy, a series of overlapping lesions 44-44''' (FIGS. 13A-13D) or a single continuous lesion can then be generated.

It will further be appreciated that the dimensional tolerances therebetween should be sufficiently large to enable smooth relative advancement and retraction of the energy delivery portion 27 around curvilinear geometries, and further enable the passage of gas therebetween. Since the ablation lumen 25 of the ablation sheath 22 is closed ended, gases must be permitted to flow between the energy delivery portion 27 and the interior wall 62 defining the ablation lumen 25 to avoid the compression of gas during advancement of the energy delivery portion therethrough. Moreover, the tolerance must be sufficiently small to substantially prevent axial rotation of the energy delivery portion in the ablation lumen 25 for alignment purposes. The dimensional tolerance between the transverse cross-sectional periphery of the ablation lumen and that of the substantially conforming energy delivery portion 27, for instance, should be in the range of about 0.001 inches to about 0.005 inches.

To further facilitate preservation of the fluids and tissues along the backside of the ablation sheath 22 (i.e., the side opposite the contact surface 23 of the sheath), a thermal isolation component (not shown) is disposed longitudinally along, and substantially adjacent to, the ablation lumen 25. Thus, during activation of the ablative device, the isolation component and the directive component 73 of the energy ablation portion 27 cooperate to form a thermal barrier along the backside of the ablation sheath.

For instance, the isolation component may be provided by an air filled isolation lumen extending longitudinally along, and substantially adjacent to, the ablation lumen 25. The cross-sectional dimension of the isolation lumen may be C-shaped or crescent shaped to partially surround the ablation lumen 25. In another embodiment, the isolation lumen may be filled with a thermally refractory material.

In still another embodiment, a circulating fluid, which is preferably biocompatible, may be disposed in the isolation lumen to provide to increase the thermal isolation. Two or more lumens may be provided to increase fluid flow. One such biocompatible fluid providing suitable thermal properties is saline solution.

Similar to the composition of the guide sheath 52, the ablation sheath 22 is composed of a flexible bio-compatible material, such as PU Pellethane, Teflon or polyethylent, which is capable of shape retention once external forces acting on the sheath are removed. By way of example, when the distal portions of the ablation sheath 22 are advanced past the interior walls of the guide lumen 54 of the guide sheath 52, the ablation sheath 22 will return to its preformed shape in the interior of the Heart.

To facilitate shape retention, the ablation sheath 22 preferably includes a shape retaining member 63 extending longitudinally through the distal portions of the ablation sheath where shape retention is necessary. As illustrated in FIGS. 1, 8 and 9, this retaining member 63 is generally extends substantially parallel and adjacent to the ablation lumen 25 to reshape the predetermined contact surface 23 to its desired pre-shaped form once the restraining forces are removed from the sheath. While this shape-memory material must be sufficiently resilient for shape retention, it must also be sufficiently bendable to enable insertion through the guide lumen 54 of the guide sheath 52. In the preferred form, the shape retaining member is composed of a superelastic metal, such as Nitinol (NiTi). Moreover, the preferred diameter of this material should be in the range of 0.020 inches to about 0.050 inches, and more preferably about 0.035 inches.

When used during a surgical procedure, the ablation sheath 22 is preferably transparent which enables a surgeon to visualize the position of the energy delivery portion 27 of the ablative device 26 through an endoscope or the like. Moreover, the material of ablation sheath 22 must be substantially unaffected by the ablative energy emitted by the energy delivery portion 27. Thus, as will be apparent, depending upon the type of energy delivery portion and the ablative source applied, the material of the tubular sheath must exhibit selected properties, such as a low loss tangent, low water absorption or low scattering coefficient to name a few, to be unaffected by the ablative energy.

As previously indicated, the ablation sheath 22 is advanced and oriented, relative to the guide sheath 52, adjacent to or into contact with the targeted tissue region 21 to form a series of over-lapping lesions 44-44''', such as those illustrated in FIGS. 3 and 13A-13D. Preferably, the contact surface 23 of the pre-shaped ablation sheath 22 is negotiated into physical contact with the targeted tissue 21. Such contact increases the precision of the tissue ablation while further facilitating energy transfer between the ablation element and the tissue to be ablated, as will be discussed.

To assess proper contact and positioning of the contact surface 23 of the ablation sheath 22 against the targeted tissue 21, at least one positioning electrode, generally designated 64, is disposed on the exterior surface of the ablation sheath for contact with the tissue. Preferably a plurality of electrodes are positioned along and adjacent the contact surface 23 to assess contact of the elongated and three dimensionally shaped contact surface. These electrodes 64 essentially measure whether there is any electrical activity (or electrophysiological signals) to one or the other side of the ablation sheath 22. When a strong electrical activation signal is detected, or inter-electrode impedance is measured when two or more electrodes are applied, contact with the tissue can be assessed. Once the physician has properly situated and oriented the sheath, they may commence advancement of the energy delivery portion 27 through the ablation lumen 25. Additionally, these positioning electrodes may be applied to map the biological tissue prior to or after an ablation procedure, as well as be used to monitor the patient's condition during the ablation process.

To facilitate discussion of the above aspects of the present invention, FIG. 10 illustrates two side-by-side electrodes 64, 65 configured for sensing electrical activity in substantially one direction, in accordance with one aspect of the present invention. This electrode arrangement generally includes a pair of longitudinally extending electrode elements 66, 67 that are disposed on'the outer periphery of the ablation sheath 22. The pair of electrode elements 66, 67 are positioned side by side and arranged to be substantially parallel to one another. In general, splitting the electrode arrangement into a pair of distinct elements permits substantial improvements in the resolution of the detected electrophysiological signals. Therefore, the pair of electrode elements 66, 67 are preferably spaced apart and electrically isolated from one another. It will be appreciated, however, that only one electrode may be employed to sense proper tissue contact. It will also be appreciated that ring or coiled electrodes can also be used.

The pair of electrode elements 66, 67 are further arranged to be substantially parallel to the longitudinal axis of the ablation sheath 22. In order to ensure that the electrode elements are sensing electrical activity in substantially the same direction, the space between electrodes should be sufficiently small. It is generally believed that too large space may create problems in determining the directional position of the catheter and too small a space may degrade the resolution of the detected electrophysiological signals. By way of example, the distance between the two pair of electrode elements may be between about 0.5 and 2.0 mm.

The electrode elements 66, 67 are preferably positioned substantially proximate to the predetermined contact surface 23 of the ablation sheath 22. More preferably, the electrode elements 66, 67 are positioned just distal to the distal end of the predetermined contact surface 23 since it is believed to be particularly useful to facilitate mapping and monitoring as well as to position the ablation sheath 22 in the area designated for tissue ablation. For example, during some procedures, a surgeon may need to ascertain where the distal end of the ablation sheath 22 is located in order to ablate the appropriate tissues. In another embodiment, the electrode elements 66, 67 may be positioned substantially proximate the proximal end of the predetermined contact surface 23, at a central portion of the contact surface 23 or a combination thereof. For instance, when attempting to contact the loop-shaped ablation sheath 22 employed to isolate each of left and inferior pulmonary vein orifices 37, 38, a central location of the electrodes along the looped-shape contact surface 23 may best sense contact with the targeted tissue. Moreover, while not specifically illustrated, a plurality of electrode arrangements may be disposed along the ablation sheath as well. By way of example, a first set of electrode elements may be disposed distally from the predetermined contact surface, a second set of electrode elements may be disposed proximally to the contact surface, while a third set of electrode elements may be disposed centrally thereof. These electrodes may also be used with other types of mapping electrodes, for example, a variety of suitable mapping electrode arrangements are described in detail in U.S. Pat. No. 5,788,692 to Campbell, et al., which is incorporated herein by reference in its entirety. Although only a few positions have been described, it should be understood that the electrode elements may be positioned in any suitable position along the length of the ablation sheath.

The electrode elements 66, 67 may be formed from any suitable material, such as stainless steel and iridium platinum. The width (or diameter) and the length of the electrode may vary to some extent based on the particular application of the catheter and the type of material chosen. Furthermore, in the preferred embodiment where microwave is used as the ablative energy, the electrodes are preferably dimensioned to minimize electromagnetic field interference, for example, the capturing of the microwave field produced by the antenna. In most embodiments, the electrodes are arranged to have a length that is substantially larger than the width, and are preferably between about 0.010 inches to about 0.025 inches and a length between about 0.50 inch to about 1.0 inch.

Although the electrode arrangement has been shown and described as being parallel plates that are substantially parallel to the longitudinal axis of the ablation sheath 22 and aligned longitudinally (e.g., distal and proximal ends match up), it should be noted that this is not a limitation and that the electrodes can be configured to be angled relative to the longitudinal axis of the ablation sheath 22 (or one another) or offset longitudinally. Furthermore, although the electrodes have been shown and described as a plate, it should be noted that the electrodes may be configured to be a wire or a point such as a solder blob.

Each of the electrode elements 66, 67 is electrically coupled to an associated electrode wire 68, 70 and which extend through ablation sheath 22 to at least the proximal portion of the flexible outer tubing. In most embodiments, the electrode wires 68, 70 are electrically isolated from one another to prevent degradation of the electrical signal, and are positioned on opposite sides of the retaining member 63. The connection between the electrodes 64, 65 and the electrode wires 68, 70 may be made in any suitable manner such as soldering, brazing, ultrasonic welding or adhesive bonding. In other embodiments, the longitudinal electrodes can be formed from the electrode wire itself. Forming the longitudinal electrodes from the electrode wire, or out of wire in general, is particularly advantageous because the size of wire is generally small and therefore the longitudinal electrodes elements may be positioned closer together thereby forming a smaller arrangement that takes up less space. As a result, the electrodes may be positioned almost anywhere on a catheter or surgical tool. These associated electrodes are described in greater detail in U.S. patent application Ser. No. 09/548,331, filed Apr. 12, 2000, and entitled "ELECTRODE ARRANGE-MENT FOR USE IN A MEDICAL INSTRUMENT", and incorporated by reference.

Referring now to FIGS. 1, 8, 9 and 11, the ablative device 26 is preferably in the form of an elongated member, which is designed for insertion into the ablation lumen 25 of the ablation sheath 22, and which in turn is designed for insertion into a vessel (such as a blood vessel) in the body of a patient. It will be understood, however, that the present invention may be in the form of a handheld instrument for use in open surgical or minimally invasive procedures (FIG. 12).

The ablative device 26 typically includes a flexible outer tubing 71 (having one or several lumens therein), a transmission line 72 that extends through the flexible tubing 71 and an energy delivery portion 27 coupled to the distal end of the transmission line 72. The flexible outer tubing 71 may be made of any suitable material such as medical grade polyolefins, fluoropolymers, or polyvinylidene fluoride. By way of example, PEBAX resins from Autochem of Germany have been used with success for the outer tubing of the body of the catheter.

In accordance with another aspect of the present invention, the ablative energy emitted by the energy delivery portion 27 of the ablative device 26 may be one of several types. Preferably, the energy delivery portion 27 includes a microwave component which generates a electromagnetic field sufficient to cause tissue ablation. As mentioned, as will be discussed in greater detail below, the ablative energy may also be derived from a laser source, a cryogenic source, an ultrasonic source or a radiofrequency source, to name a few.

Regardless of the source of the energy, a directive component cooperates with the energy source to control the direction and emission of the ablative energy. This assures that the surrounding tissues of the targeted tissue regions will be preserved. Further, the use of a directional field has several potential advantages over conventional energy delivery structure that generate uniform fields about the longitudinal axis of the energy delivery portion. For example, in the microwave application, by forming a more concentrated and directional electromagnetic field, deeper penetration of biological tissues is enabled, and the targeted tissue region may be ablated without heating as much of the surrounding tissues and/or blood. Additionally, since substantial portions the radiated ablative energy is not emitted in the air or absorbed in the blood or the surrounding tissues, less power is generally required from the power source, and less power is generally lost in the microwave transmission line.

In the preferred form, the energy delivery portion 27 of the ablative device 26 is an antenna assembly configured to directionally emit a majority of an electromagnetic field from one side thereof. The antenna assembly 27, as shown in FIGS. 9 and 11, preferably includes a flexible antenna 60, for generating the electromagnetic field, and a flexible reflector 73 as a directive component, for redirecting a portion of the electromagnetic field to one side of the antenna opposite the reflector. Correspondingly, the resultant electromagnetic field includes components of the originally generated field, and components of the redirected electromagnetic field. During aligned insertion of the antenna assembly 27 into the ablation lumen 25, via the key structure 48, the directional field will thus be continuously aligned toward the contact surface 23 of the ablation sheath 22 as the antenna assembly is incrementally advanced through the ablation lumen 25.

FIG. 11 illustrates that the proximal end of the antenna 60 is preferably coupled directly or indirectly to the inner conductor 75 of a coaxial transmission line 72. A direct connection between the antenna 60 and the inner conductor 75 may be made in any suitable manner such as soldering, brazing, ultrasonic welding or adhesive bonding. In other embodiments, antenna 60 can be formed from the inner conductor 75 of the transmission line 72 itself. This is typically more difficult from a manufacturing standpoint but has the advantage of forming a more rugged connection between the antenna and the inner conductor. As will be described in more detail below, in some implementations, it may be desirable to indirectly couple the antenna to the inner conductor through a passive component, such a capacitor, an inductor or a stub tuner for example, in order to provide better impedance matching between the antenna assembly and the transmission line, which is a coaxial cable in the preferred embodiment.

Briefly, the transmission line 72 is arranged for actuating and/or powering the antenna 60. Typically, in microwave devices, a coaxial transmission line is used, and therefore, the transmission line 72 includes an inner conductor 75, an outer conductor 76, and a dielectric material 77 disposed between the inner and outer conductors. In most instances, the inner conductor 75 is coupled to the antenna 60. Further, the antenna 60 and the reflector 73 are enclosed (e.g., encapsulated) in a flexible insulative material thereby forming the insulator 61, to be described in greater detail below, of the antenna assembly 27.

The power supply (not shown) includes a microwave generator which may take any conventional form. When using microwave energy for tissue ablation, the optimal frequencies are generally in the neighborhood of the optimal frequency for heating water. By way of example, frequencies in the range of approximately 800 MHz to 6 GHz work well. Currently, the frequencies that are approved by the Federal Communication Commission (FCC) for experimental clinical work includes 915 MHz and 2.45 GHz. Therefore, a power supply having the capacity to generate microwave energy at frequencies in the neighborhood of 2.45 GHz may be chosen. A conventional magnetron of the type commonly used in microwave ovens is utilized as the generator. It should be appreciated, however, that any other suitable microwave power source could be substituted in its place, and that the explained concepts may be applied at other frequencies like about 434 MHz or 5.8 GHz (ISM band).

In the preferred embodiment, the antenna assembly 27 includes a longitudinally extending antenna wire 60 that is laterally offset from the transmission line inner conductor 75 to position the antenna closer to the window portion 58 of the insulator 61 upon which the directed electric field is transmitted. The antenna 60 illustrated is preferably a longitudinally extending exposed wire that extends distally (albeit laterally offset) from the inner conductor. However it should be appreciated that a wide variety of other antenna geometries may be used as well. By way of example, helical coils, flat printed circuit antennas and other antenna geometries will work as well.

Briefly, the insulator 61 is preferably provided by a good, low-loss dielectric material which is relatively unaffected by microwave exposure, and thus capable of transmission of the electromagnetic field therethrough. Moreover, the insulator material preferably has a low water absorption so that it is not itself heated by the microwaves. Incidentally, when the emitted ablative energy is microwave in origin, the ablation sheath must also include these material properties. Finally, the insulation material must be capable of substantial flexibility without fracturing or breaking. Such materials include moldable TEFLON®, silicone, or polyethylene, polyimide, etc.

As will be appreciated by those familiar with antenna design, the field generated by the illustrated antenna will be generally consistent with the length of the antenna. That is, the length of the electromagnetic field is generally constrained to the longitudinal length of the antenna. Therefore, the length of the field may be adjusted by adjusting the length of the antenna. Accordingly, microwave ablation elements having specified ablation characteristics can be fabricated by building them with different length antennas. Additionally, it should be understood that longitudinally extending antennas are not a requirement and that other shapes and configurations may be used.

The antenna 60 is preferably formed from a conductive material. By way of example, copper or silver-plated metal work well. Further, the diameter of the antenna 60 may vary to some extent based on the particular application of the catheter and the type of material chosen. In microwave systems using a simple exposed wire type antenna, for instance, wire diameters between about 0.010 to about 0.020 inches work well. In the illustrated embodiment, the diameter of the antenna is about 0.013 inches.

In a preferred embodiment, the antenna 60 is positioned closer to the area designated for tissue ablation in order to achieve effective energy transmission between the antenna 60 and the targeted tissue 21 through the predetermined contact surface 23 of the ablation sheath 22. This is best achieved by placing the antenna 60 proximate to the outer peripheral surface of the antenna insulator 61. More specifically, a longitudinal axis of the antenna 60 is preferably off-set from, but parallel to, a longitudinal axis 78 of the inner conductor 75 in a direction away from the reflector 73 and therefore towards the concentrated electromagnetic field (FIGS. 8 and 9). By way of example, placing the antenna between about 0.010 to about 0.020 inches away from the outer peripheral surface of the antenna insulator works well. In the illustrated embodiment, the antenna is about 0.013 inches away from the outer peripheral surface of the antenna insulator 61. However, it should be noted that this is not a requirement and that the antenna position may vary according to the specific design of each catheter.

Referring now to the directive component or reflector 73, it is positioned adjacent and generally parallel to a first side of the antenna, and is configured to redirect those components of the electromagnetic field contacting the reflector back towards and out of a second side of the antenna assembly 27 opposite the reflector. A majority of the electromagnetic field, consequently, is directed out of the window portion 58 of the insulator 61 in a controlled manner during ablation.

To reduce undesirable electromagnetic coupling between the antenna and the reflector 73, the antenna 60 is preferably off-set from the reflector 73 (FIGS. 8 and 9). This off-set from the longitudinal axis 78 further positions the antenna 60 closer to the window portion 58 to facilitate ablation by positioning the antenna 60 closer to the targeted tissue region. It has been found that the minimum distance between the reflector and the antenna may be between about 0.020 to about 0.030 inches, in the described embodiment, in order to reduce the coupling. However, the distance may vary according to the specific design of each ablative device.

The proximal end of the reflector 73 is preferably coupled to the outer conductor 76 of the coaxial transmission line 72. Connecting the reflector to the outer conductor serves to better define the electromagnetic field generated during use. That is, the radiated field is better confined along the antenna, to one side, when the reflector is electrically connected to the outer conductor of the coaxial transmission line. The connection between the reflector 73 and the outer conductor 76 may be made in any suitable manner such as soldering, brazing, ultrasonic welding or adhesive bonding. In other embodiments, the reflector can be formed from the outer conductor of the transmission line itself. This is typically more difficult from a manufacturing standpoint but has the advantage of forming a more rugged connection between the reflector and the outer conductor.

In one embodiment, to improve flexibility at the electrical connection with the outer conductor 76 and entirely along the energy delivery device, the proximal end of the reflector 73 is directly contacted against the outer conductor without applying solder or such conductive-adhesive bonding. In this design, the insulator material of the insulator 61 functions as the adhesive to maintain electrical continuity. This is performed by initially molding the antenna wire in the silicone insulator. The reflector 73 is subsequently disposed on the molded silicone tube, and is extended over the outer conductor 76 of coaxial cable transmission line 72. A heat shrink tube is then applied over the assembly to firmly maintain the electrical contact between the reflector 73 and the coaxial cable outer conductor 76. In other embodiments, the reflector may be directly coupled to a ground source or be electrically floating.

As previously noted, the antenna 60 typically emits an electromagnetic field that is fairly well constrained to the length of the antenna. Therefore, in some embodiments, the distal end of the reflector 73 extends longitudinally to at about the distal end of the antenna 60 so that the reflector can effectively cooperate with the antenna. This arrangement serves to provide better control of the electromagnetic field during ablation. However, it should be noted that the actual length of the reflector may vary according to the specific design of each catheter. For example, catheters having specified ablation characteristics can be fabricated by building catheters with different length reflectors.

Furthermore, the reflector 73 is typically composed of a conductive, metallic material or foil. However, since the antenna assembly 27 must be relatively flexible in order to negotiate the curvilinear ablation lumen 25 of the ablation sheath 22 as the ablative device it is advanced therethrough, the insulator 61, the antenna wire and the reflector must collectively be relatively flexible. Thus, one particularly material suitable for such a reflector is a braided conductive mesh having a proximal end conductively mounted to the distal portion of the outer conductor of the coaxial cable. This conductive mesh is preferably thin walled to the shield assembly yet provide the appropriate microwave shielding properties, as well as enable substantial flexibility of the shield device during bending movement. For example, a suitable copper mesh wire should have a diameter in the range of about 0.005 inches to about 0.010 inches, and more preferably about 0.007 inches. A good electrical conductor is generally used for the shield assembly in order to reduce the self-heating caused by resistive losses. Such conductors includes, but are not restricted to copper, silver and gold.

Another suitable arrangement may be thin metallic foil reflector 73 which is inherently flexible. However, to further increase flexibility, the foil material can be pleated or folded which resists tearing during bending of the antenna assembly 27. These foils can be composed of copper that has a layer of silver plating formed on its inner peripheral surface. Such silver plating, which can also be applied to the metallic mesh material, is used to increase the conductivity of the reflector. It should be understood, however, that these materials are not a limitation. Furthermore, the actual thickness of the reflector may vary according to the specific material chosen.

Referring back to FIG. 11, the reflector 73 is preferably configured to have an arcuate or meniscus shape (e.g., crescent), with an arc angle that opens towards the antenna 60. Flaring the reflector towards the antenna serves to better define the electromagnetic field generated during use. Additionally, the reflector functions to isolate the antenna 60 from the restraining member 63 of the ablation sheath 22 during ablation. Since the restraining member 63 is preferably metallic in composition (most preferably Nitinol), it is desirable minimize electromagnetic coupling with the antenna. Thus, the reflector 73 is preferably configured to permit at most a 180° circumferential radiation pattern from the antenna. In fact, it has been discovered that arc angles greater than about 180° are considerably less efficient. More preferably, the arc angle of the radiation pattern is in the range of about 90° to about 120°.

While the reflector is shown and described as having an arcuate shape, it will be appreciated that a plurality of forms may be provided to accommodate different antenna shapes or to conform to other external factors necessary to complete a surgical procedure. For example, any flared shape that opens towards the antenna may work well, regardless of whether it is curvilinear or rectilinear.

Further still, it should be noted that the shape of the reflector need not be uniform. For example, a first portion of the reflector (e.g., distal) may be configured with a first shape (e.g., 90° arc angle) and a second portion (e.g., proximal) of the reflector may be configured with a second shape (e.g., 120° arc angle). Varying the shape of the reflector in this manner may be desirable to obtain a more uniform radiated field. It is believed that the energy transfer between the antenna and the tissue to be ablated tends to increase by decreasing the coverage angle of the reflector, and conversely, the energy transfer between the antenna and the tissue to be ablated tends to decrease by increasing the coverage angle of the reflector. Accordingly, the shape of the reflector may be altered to balance out non-uniformities found in the radiated field of the antenna arrangement.

In another configuration, the directive component 73 for the microwave antenna assembly 27 can be provided by another dielectric material having a dielectric constant different than that of the insulator material 67. Indeed, a strong reflection of electromagnetic wave is observed when the wave reaches an interface created by two materials with a different dielectric constant. For example, a ceramic loaded polymer can have a dielectric constant comprised between 15 and 55, while the dielectric of a fluoropolymer like Teflon or is comprised between 2 and 3. Such an interface would create a strong reflection of the wave and act as a semi-reflector.

It should also be noted that the longitudinal length of the reflector need not be uniform. That is, a portion of the reflector may be stepped towards the antenna or a portion of the reflector may be stepped away from the antenna. Stepping the reflector in this manner may be desirable to obtain a more uniform radiated field. While not wishing to be bound by theory, it is believed that by placing the reflector closer to the antenna, a weaker radiated field may be obtained, and that by placing the reflector further away from the antenna, a stronger radiated field may be obtained. Accordingly, the longitudinal length of the reflector may be altered to balance out non uniformities found in the radiated field of the antenna arrangement. These associated reflectors are described in greater detail in U.S. patent application Ser. No. 09/178,066, entitled "DIRECTIONAL REFLECTOR SHIELD ASSEMBLY FOR A MICROWAVE ABLATION INSTRUMENT, and Ser. No. 09/484,548 entitled "A MICROWAVE ABLATION INSTRUMENT WITH FLEXIBLE ANTENNA ASSEMBLY AND METHOD", each of which is incorporated by reference.

In a typical microwave ablation system, it is important to match the impedance of the antenna with the impedance of the transmission line. As is well known to those skilled in the art, if the impedance is not matched, the catheter's performance tends to be well below the optimal performance. The decline in performance is most easily seen in an increase in the reflected power from the antenna toward the generator. Therefore, the components of a microwave transmission system are typically designed to provide a matched impedance. By way of example, a typical set impedance of the microwave ablation system may be on the order of fifty (50) ohms.

Referring back to FIGS. 10 and 11, and in accordance with one embodiment of the present invention, an impedance matching device 80 may be provided to facilitate impedance matching between the antenna 60 and the transmission line 72. The impedance matching device 80 is generally disposed proximate the junction between the antenna 60 and the inner conductor 75. For the most part, the impedance match is designed and calculated assuming that the antenna assembly 27, in combination with the predetermined contact surface 23 of the ablation sheath 22, is in resonance to minimize the reflected power, and thus increase the radiation efficiency of the antenna structure.

In one embodiment, the impedance matching device is determined by using a Smith Abacus Model. In the Smith Abacus Model, the impedance matching device may be ascertained by measuring the impedance of the antenna with a network analyzer, analyzing the measured value with a Smith Abacus Chart, and selecting the appropriate device. By way of example, the impedance matching device may be any combination of a capacitor, resistor, inductor, stub tuner or stub transmission line, whether in series or in parallel with the antenna. An example of the Smith Abacus Model is described in Reference: David K. Cheng, "Field and Wave Electromagnetics," second edition, Addison-Wesley Publishing, 1989, which is incorporated herein by reference. In one preferred implementation, the impedance matching device is a serial capacitor having a capacitance in the range of about 0.6 to about 1.0 Pico Farads. In the illustration shown, the serial capacitor has a capacitance of about 0.8 Pico Farads.

As above-mentioned, the impedance will be matched assuming flush contact between the antenna assembly 27 and the ablation sheath (FIG. 9). In accordance with the present invention, as the antenna assembly 27 is advanced through the ablation lumen 25, before selective ablation, it is desirable to position the window portion 58 of the flexible antenna insulator 61 in flush contact against the interior wall 62 of the ablation lumen 25, opposite the predetermined contact surface 23. This arrangement may substantially reduce the impedance variance caused by the interface between insulator 61 and the ablation sheath 22 as the directional field is transmitted therethrough. In comparison, if the window portion 58 were not required to be positioned in flush contact against the interior wall 62 of the ablation lumen, pockets of air or fluid, or the like, may be disposed intermittently therebetween which would result in a greater degree of impedance variations at this interface. Consequently, the above-indicated impedance matching techniques would be less effective.

To assure such flush contact during selective directional ablation and advancement along the sheath ablation lumen, the ablation system 20 preferably incorporates a forcing mechanism 81 (FIGS. 8 and 9) adapted to urge the window portion 58 of the antenna assembly 27 into flush contact against the interior wall 62 of the ablation sheath. Preferably, the forcing mechanism cooperates between a support portion 82 of the interior wall 62 of the ablation lumen 25 and the forcing wall portion 83 of the antenna assembly.

When not operational, the forcing mechanism permits relative axial displacement between the ablative device 26 and the ablation sheath for repositioning of the antenna assembly 27 along the ablation path 28 (FIG. 8). Upon selective operation, the forcing mechanism 81 contacts the forcing wall portion 83 to urge window portion 58 flush against the interior wall 62 opposite the predetermined contact surface 23. Consequently, the impedance match between the antenna and the transmission line is properly achieved and stable even when the antenna is moving in the ablation sheath.

In one embodiment, the forcing mechanism may be provided by an inflatable structure acting between the support portion 82 of the interior wall 62 of the ablation lumen 25 and the forcing wall portion 83 of the antenna assembly device. Upon selective inflation of forcing mechanism 81 (FIG. 9), the window portion 58 will be urged into flush contact with the interior wall 62 of the ablation lumen. Upon selective deflation of the forcing mechanism 81 (FIG. 8), relative axial displacement between the antenna assembly 27 and the ablation sheath may commence. The forcing mechanism can be provided by other techniques such as spring devices or the like.

In accordance with another aspect of the present invention, the ablative energy may be in the form of laser energy sufficient to ablate tissue. Example of such laser components include $CO_2$ or Nd: YAG lasers. To transmit the beams, the transmission line 72 is preferably in the form of a fiber optic cable or the like.

Figure 14A:
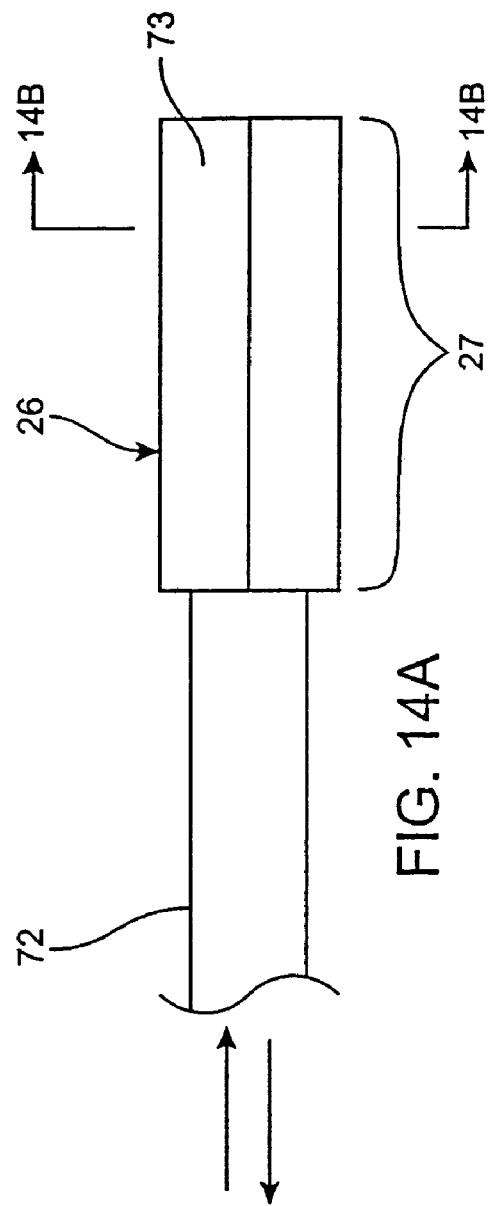
FIG. 14A is a fragmentary, side elevation view of a laser-type ablation device of the present invention.
Figure 14B:
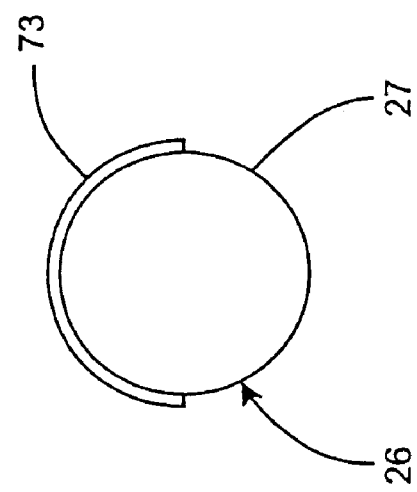
FIG. 14B is a front elevation view of the laser-type energy delivery portion taken along the plane of the line 14B-14B in FIG. 14A.

In this design, as shown in FIGS. 14A and 14B, the directive component 73 may be provided by a reflector having a well polished smooth reflective or semi-reflective surface. This preferably metallic reflective surface is configured to reflect the emitted laser energy toward the targeted tissue region. By way of example, functional metallic materials include silver or platinum. In another configuration, similar to the difference in dielectric constants of the microwave ablation device 26, the directive component of the laser ablative device may be provided between two layers of dielectric materials with a sufficient difference between the refractory indexes. Here, at least one dielectric directive component layer functions like the outer dielectric layer of the fiber optic transmission line 72 to obtain "total internal reflection". Consequently, the laser energy can be emitted away fro'm the dielectric layer. By providing more than one dielectric layer, "total internal reflection" may be attained at several angles of incidence. Again, the reflection of the electromagnetic wave is caused by the interface between two media having different dielectric constants. Generally speaking, the higher is the difference between the dielectric constants, the more significant is the internal reflection. In addition, when more than one dielectric layer are involved, interference can be used to direct the laser energy in a preferred direction.

Moreover, when the ablative energy is laser based, it will be appreciated that it is desirable that both the ablation sheath 22 and the ablation device be composed of materials which have a low scattering coefficient and a low factor of absorption. In addition, it is also preferable to use material with low water absorption.

It will be appreciated that a plurality of designs can be used for the laser energy delivery portion. For example, the laser energy delivery portion can consist of multiple reflective particles embedded in a laser transparent material. The laser wave is propagating from the laser generator to the optic fiber transmission line and enter in the laser energy delivery portion. The embedded reflective particles diffracts the light, which is reflected toward the tissue to be ablated by the directive component 73.

Figure 15A:
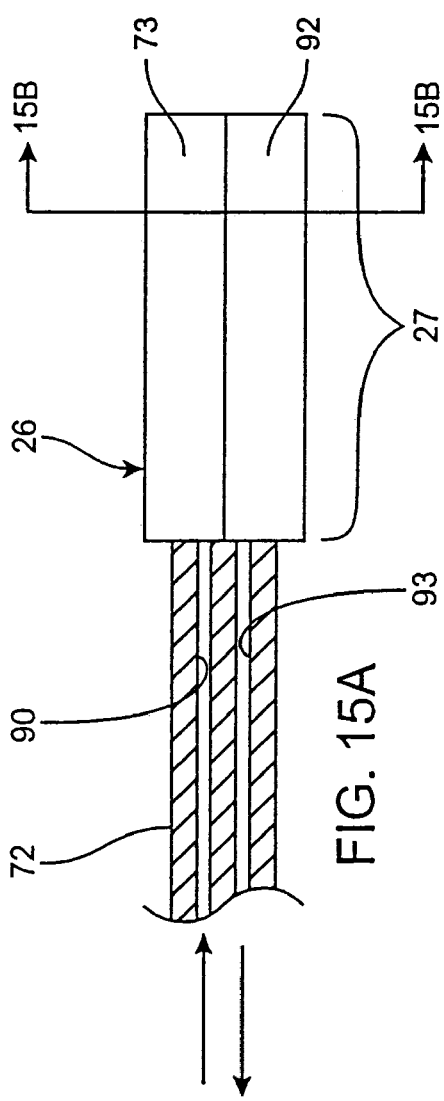
FIG. 15A is a fragmentary, side elevation view of a cryogenic-type ablation device of the present invention.
Figure 15B:
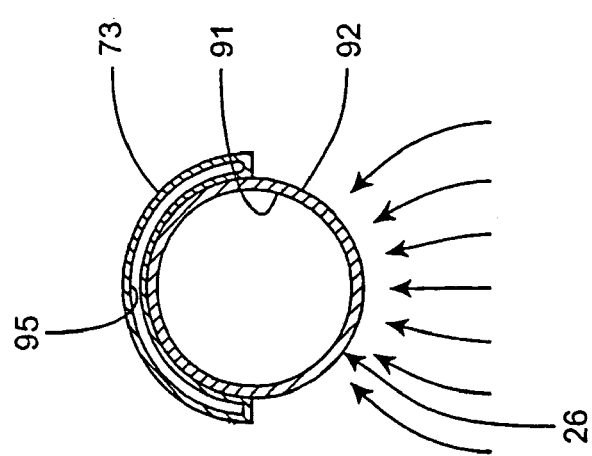
FIG. 15B is a front elevation view of the cryogenic-type energy delivery portion taken along the plane of the line 15B-15B in FIG. 15A.

In yet another alternative embodiment, cryogenic energy may be employed as an ablative energy. Briefly, as shown in FIGS. 15A and 15B, in these cryogenic ablation device designs, a cryogenic fluid, such as a pressurized gas (like Freon for example) is passed through an inflow lumen 90 in the ablation device transmission line 72. The distal ablative device 26 is preferably provided by a decompression chamber which decompresses the pressurized gas from the inflow lumen 90 therein. Upon decompression or expansion of the pressurized gas in the decompression chamber 91, the temperature of the exterior surface 92 of the decompression chamber is sufficiently reduced to cause tissue ablation upon contact thereof. The decompressed gas is then exhausted through the outflow lumen 93 of the transmission line 72.

FIG. 15B illustrates that the directive component 73 is in the form of a thermal insulation layer extending longitudinally along one side of the energy delivery portion 27. By forming a good thermal insulator with a low thermal conductivity, the C-shaped insulation layer 73 will substantially minimize undesirable cryogenic ablation of the immediate tissue surrounding of the targeted tissue region. In one configuration, the isolation layer may define a thin, elongated gap 95 which partially surrounds the decompression chamber 91. This gap 95 may then be filled with air, or an inert gas, such as $CO_2$, to facilitate thermal isolation. The isolation gap 95 may also be filled with a powder material having relatively small solid particulates or by air expended polymer. These materials would allow small air gaps between the insulative particles or polymeric matrix for additional insulation thereof. The isolation layer may also be provided by a refractory material. Such materials forming an insulative barrier include ceramics, oxides, etc.

Figure 16:
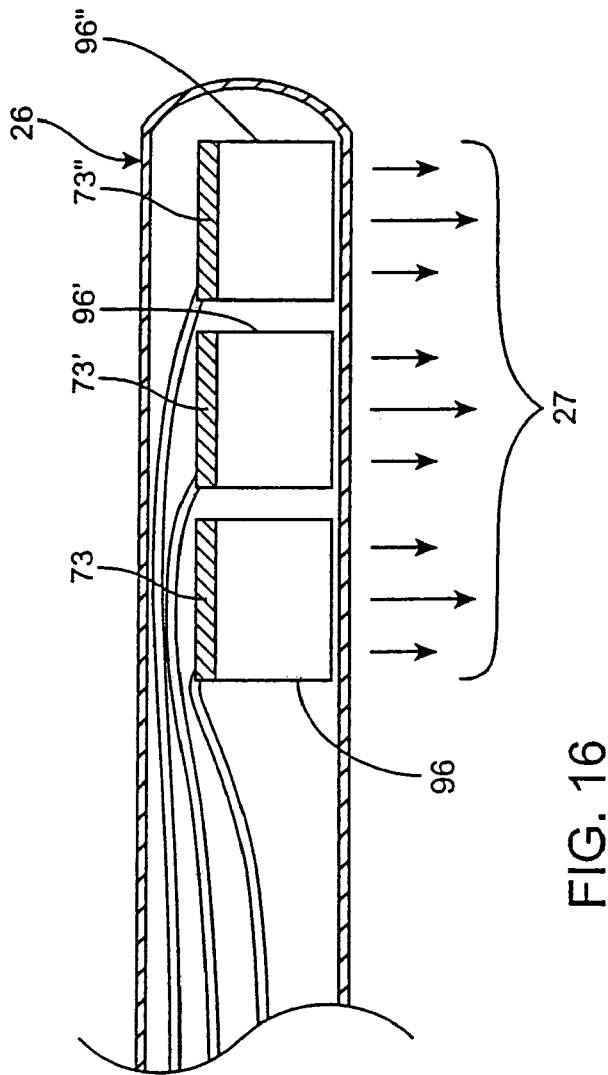
FIG. 16 is a fragmentary, side elevation view, in cross-section, of an ultrasonic-type ablation device of the present invention.

Referring now to FIG. 16, an ultrasound ablation device may also be applied as another viable source of ablation energy. For example, a piezoelectric transducer 96 may be supplied as the ablative element which delivers acoustic waves sufficient to ablate tissue. These devices emit ablative energy which can be directed and shaped by applying a directive echogenic component to reflect the acoustic energy. Moreover, a series or array of piezoelectric transducers 96, 96' and 96" can be applied to collectively form a desired radiation pattern for tissue ablation. For example, by adjusting the delay between the electrical exciting signal of one transducer and its neighbor, the direction of transmission can be modified. Typical of these transducers include piezoelectric materials like quartz, barium oxides, etc.

In this configuration, the directive component 73 of the ultrasonic ablation device may be provided by an echogenic material (73-73') positioned proximate the piezoelectric transducers. This material reflects the acoustic wave and which cooperates with the transducers to direct the ablative energy toward the targeted tissue region. By way of example, such echogenic materials are habitually hard. They include, but are not restricted to metals and ceramics for example.

Moreover, when the ablative energy is ultrasonic based, it will be appreciated that it is desirable that both the ablation sheath 22 and the ablation device be composed of materials which have low absorption of the acoustic waves, and that provide a good acoustic impedance matching between the tissue and the transducer. In that way, the thickness and the material chosen for the ablation sheath play in important role to match the acoustic properties of the tissue to be ablated and the transducer. An impedance matching jelly can also be used in the ablation sheath to improve the acoustic impedance matching.

Lastly, the ablation device may be provided by a radiofrequency (RF) ablation source which apply RF conduction current sufficient to ablate tissue. These conventional ablation instruments generally apply conduction current in the range of about 450 kHz to about 550 kHz. Typical of these RF ablation devices include ring electrodes, coiled electrodes or saline electrodes.

To selectively direct the RF energy, the directive component is preferably composed of an electrically insulative and flexible material, such as plastic or silicone. These biocompatible materials perform the function of directing the conduction current toward a predetermined direction.

In an alternative embodiment, as best viewed in FIG. 17, the window portion 58 of the ablation sheath 22 is provided by an opening in the sheath along the ablation path, as opposed to being merely transparent to the energy ablation devices. In this manner, when the ablation sheath 22 is properly positioned with the window portion placed proximate and adjacent the targeted tissue, the energy delivery portion 27 of the ablation device 26 may be slidably positioned into direct contact with the tissue for ablation thereof. Such direct contact is especially beneficial when it is technically difficult to find a sheath that is merely transparent to the used ablative energy. For example, it would be easier to use a window portion when RF energy is used. The ablative RF element could directly touch the tissue to be ablated while the directive element would be the part of the ablation sheath 22 facing away the window portion 58. Furthermore, during surgical ablation, the window portion could be used by the surgeon to indicate the area where an ablation can potentially be done with the energy ablation device.

In yet another embodiment, the ablation system 20 may be in the form of a rail system including a rail device 96 upon which the ablation device 26 slides therealong as compared to therethrough. FIGS. 18 and 19 illustrate the rail device 96 which is preferably pre-shaped or bendable to proximately conform to the surface of the targeted tissue. Once the rail device 96 is positioned, the ablation device can be advanced or retracted along the path defined by the rail device for ablation of the targeted tissue 21.

The ablation device 26 in this arrangement includes a body portion 98 housing the energy delivery portion 27 therein. The window portion 58 is preferably extend longitudinally along the outer surface of one side of the housing. An opposite side of the housing, and longitudinally oriented substantially parallel to the window portion 58 is a rail receiving passage 97 formed and dimensioned to slidably receive and slide over the rail device 96 longitudinally therethrough. In one configuration, the energy delivery portion 27 may be advanced by pushing the body portion 98 through the transmission line 72. Alternatively, the energy delivery portion 27 may be advanced by pulling the body portion 98 along the path of the rail system 20.

As best viewed in FIG. 19, the directive component 73 of the ablation device 26 is integrally formed with the body portion 98 of the ablation device. This preferably C-shaped component extends partially peripherally around the energy delivery portion 27 to shield the rail device 96 from exposure to the ablative energy. Depending upon the type of ablative energy employed, the material or structure of the directive component 73 can be constructed as set forth above.

To assure the directional position and orientation of the window portion 58 of the ablative device toward the targeted tissue, a key structure 48 is employed. Generally, the transverse cross-sectional dimension of the rail device 96 and matching rail receiving passage 97 is shaped to assure proper directional orientation of the ablative energy. Examples of such key forms are shown in FIGS. 20A-20B.

As with the previous embodiments, the open window embodiment and the rail system embodiment may employ multiple ablative element technology. These include microwave, radiofrequency, laser, ultrasound and cryogenic energy sources.

In accordance with another aspect of the present invention, the tissue ablation system further includes a temperature sensor which is applied to measure the temperature of the ablated tissue during the ablation. In one embodiment, the temperature sensor is mounted to the ablation device proximate the energy delivery portion 27 so that the sensor moves together with the energy delivery portion as it is advanced through the ablation sheath. In another embodiment, the temperature sensor is attached on the ablation sheath.

To determine the temperature of the ablated tissue, a mathematical relationship is used to calculate the tissue temperature from the measured temperature. Typical of such temperature sensors include a metallic temperature sensor, a thermocouple, a thermistor, or a non-metallic temperature sensor such as fiber optic temperature sensor.

In accordance with the present invention, the guide sheath 52 and the ablation sheath 22 can be designed and configured to steer the ablative device along any three dimensional path. Thus, the tissue ablation system of present invention may be adapted for an abundance of uses. For instance, the distal end portion of the ablation sheath can be configured to form a closed ablation path for the ablation device. This design may be employed to ablate around an ostium of an organ, or to electrically isolate one or several pulmonary veins to treat atrial fibrillation. A closed ablation path may also utilized to ablate around an aneurysm, such as a cardiac aneurysm or tumor, or any kink of tumor. In other example, the ablation sheath can be inserted in an organ in order to ablate a deep tumor or to perform any surgical treatment where a tissue ablation is required.

In other instances, the distal end portion of the ablation sheath 22 may define a rectilinear or curvilinear open ablation path for the ablation device. Such open ablation paths may be applied to ablate on the isthmus between the inferior vena cava vein (IVC) and the tricuspid valve (TV), to treat regular flutter, or to generate a lesion between the IVC and the SVC, to avoid macro-reentry circuits in the right atrium. Other similar ablation lesions can be formed between: any of the pulmonary vein ostium to treat atrial fibrillation; the mitral valve and one of the pulmonary veins to avoid macro-reentry circuit around the pulmonary veins in the left atrium; and the left appendage and one of the pulmonary veins to avoid macro-reentry circuit around the pulmonary veins in the left atrium.

The ablation apparatus may be applied through several techniques. By way of example, the ablation apparatus may be inserted into the coronary circulation to produce strategic lesions along the endocardium of the cardiac chambers (i.e., the left atrium, the right atrium, the left ventricle or the right ventricle). Alternatively, the ablation apparatus may be inserted through the chest to produce epicardial lesions on the heart. This insertion may be performed through open surgery techniques, such as by a sternotomy or a thoracotomy, or through minimally invasive techniques, applying a cannula and an endoscope to visualize the location of the ablation apparatus during a surgery.

The ablation apparatus is also suitable for open surgery applications such as ablating the exterior surfaces of an organ as well, such as the heart, brain, stomach, esophagus, intestine, uterus, liver, pancreas, spleen, kidney or prostate. The present invention may also be applied to ablate the inside wall of hollow organs, such as heart, stomach, esophagus, intestine, uterus, bladder or vagina. When the hollow organ contains bodily fluid, the penetration port formed in the organ by the ablation device must be sealed to avoid a substantial loss of this fluid. By way of example, the seal may be formed by a purse string, a biocompatible glue or by other conventional sealing devices.

As mentioned, the present invention may be applied in an intra-coronary configuration where the ablation device is used to isolate the pulmonary vein from the left atrium. FIG. 2C illustrates that a distal end of the ablation sheath 22 is adapted for insertion into the pulmonary vein. In this embodiment, the distal end of the ablation device may include at least one electrode used to assess the electrical isolation of the vein. This is performed by pacing the distal electrode to "capture" the heart. If pacing captures the heart, the vein is not yet electrically isolated, while, if the heart cannot be captured, the pulmonary vein is electrically isolated from the left atrium. As an example, a closed annular ablation on the posterior wall of the left atrium around the ostium of the pulmonary vein by applying the pigtail ablation sheath 22 of FIGS. 2 and 4.

In yet another configuration, the ablation device may include a lumen to inject a contrasting agent into the organ. For instance, the contrasting agent facilitates visualization of the pulmonary vein anatomy with a regular angiogram technique. This is important for an intra-coronary procedure since fluoroscopy is used in this technique. The premise, of course, is to visualize the shape and the distal extremity of the sheaths, as well as the proximal and distal part of the sliding energy delivery portion during an ablative procedure under fluoroscopy. It is essential for the electrophysiologist to be able to identify not only the ablative element but also the path that the ablation sheath will provide to guide the energy delivery portion 27 therealong.

Another visualization technique may be to employ a plurality of radio-opaque markers spaced-apart along the guide sheath to facilitate location and the shape thereof. By applying the radio-opaque element that will show the shape of the sheath. This element can be a metallic ring or soldering such as platinum which is biocompatible and very radio-opaque. Another example of a radio-opaque element would be the application of a radio-opaque polymer such as a beryllium loaded material. Similarly, radio-opaque markers may be disposed along the proximal, middle and distal ends of the energy delivery portion 27 to facilitate the visualization and the location of the energy delivery portion when the procedure is performed under fluoroscopy.

To facilitate identification of the distal end portion of the ablation sheath, a fluoro-opaque element may be placed at the distal extremity. Another implementation of this concept would be to have different opacities for the ablation sheath and the energy delivery portion 27. For example, the energy delivery portion may be more opaque than that of the ablation sheath, and the ablation sheath may be more opaque than the trans-septal sheath, when the later is used.

Figure 21:
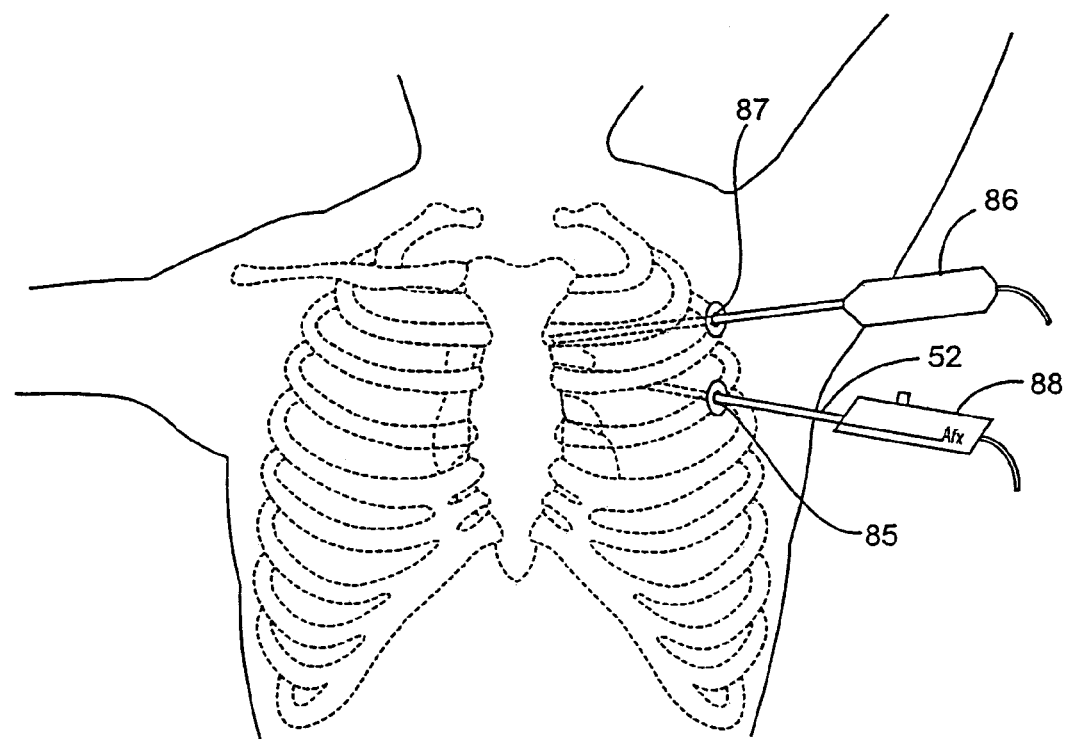
FIG. 21 is a fragmentary, diagrammatic, front elevation view of a torso applying one embodiment of the present invention through a minimally invasive technique.
Figure 22:
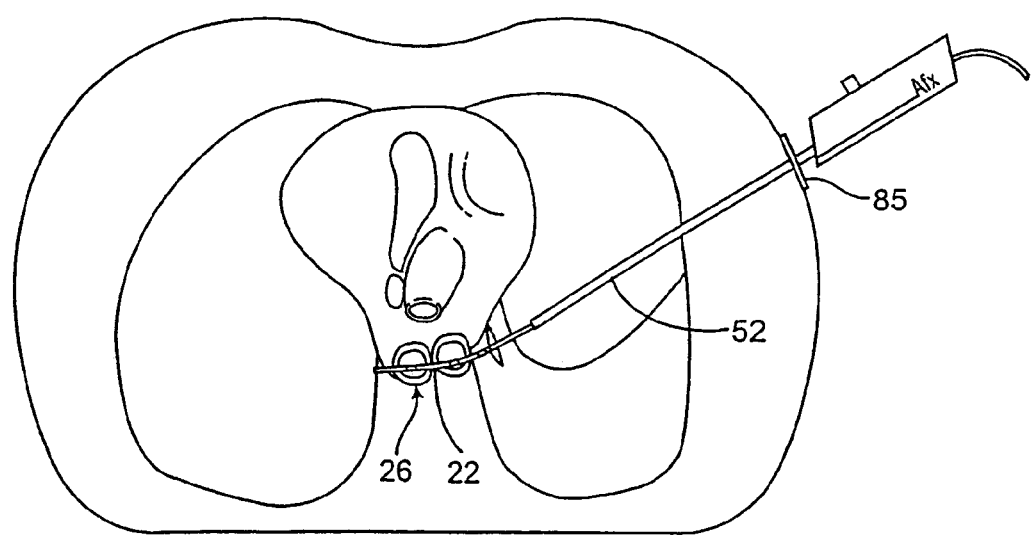
FIG. 22 is a top plan view, in cross-section of the fragmentary, diagrammatic, top plan view of the torso of FIG. 21 applying the minimally invasive technique.

The surgical ablation device of the present invention may also be applied minimally invasively to ablate the epicardium of a beating heart through an endoscopic procedure. As viewed in FIGS. 21 and 22, at least one intercostal port 85 or access port is formed in the thorax. A dissection tool (not shown) or the like may be utilized to facilitate access to the pericardial cavity. For instance, the pericardium may be dissected to enable access to the epicardium of a beating heart. The pericardial reflections may be dissected in order to allow the positioning of the ablation device 26 around the pulmonary veins. Another dissection and positioning tool 100, described in more detail below, may also be utilized to puncture the pericardial reflection located in proximity to a pulmonary vein and assist in positioning the ablation device housed therein. After the puncture of the pericardial reflection, the ablation sheath can be positioned around one, or more than one pulmonary vein in order to produce the ablation pattern used to treat the arrhythmia, atrial fibrillation in particular.

For example, a guide sheath 52 may be inserted through the access port 85 while visualizing the insertion process with an endoscopic device 86 positioned in another access port 87. Once the guide sheath 52 is properly positioned by handle 88, the ablation sheath 22 may be inserted through the guide sheath, while again visualizing the insertion process with the endoscopic system to position the ablation sheath on the targeted tissue to ablate. The ablation device may then be slid through the ablation lumen of the ablation sheath and adjacent the targeted tissue. Similar to the previous ablation techniques, the ablative element of the ablation device may be operated and negotiated in an overlapping manner to form a gap free lesion or a plurality of independent lesions. The ablation sheath may also be malleable or flexible. The surgeon can use a surgical instrument, like a forceps, to manipulate, bend and position the ablation sheath.

Figure 23D:
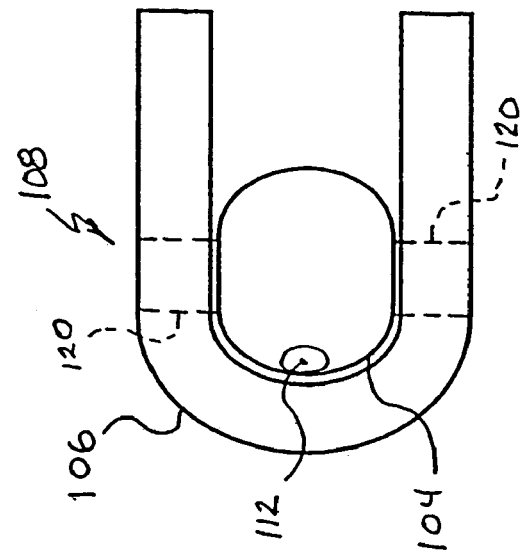
FIG. 23D is an end elevation view of an alternative embodiment of a positioning tool used in accordance with the present invention.
Figure 23C:
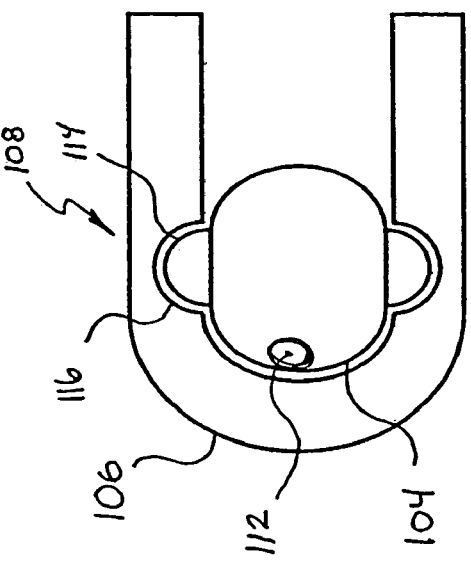
FIG. 23C is an end elevation view of a positioning tool used in accordance with the present invention.
Figure 23E:
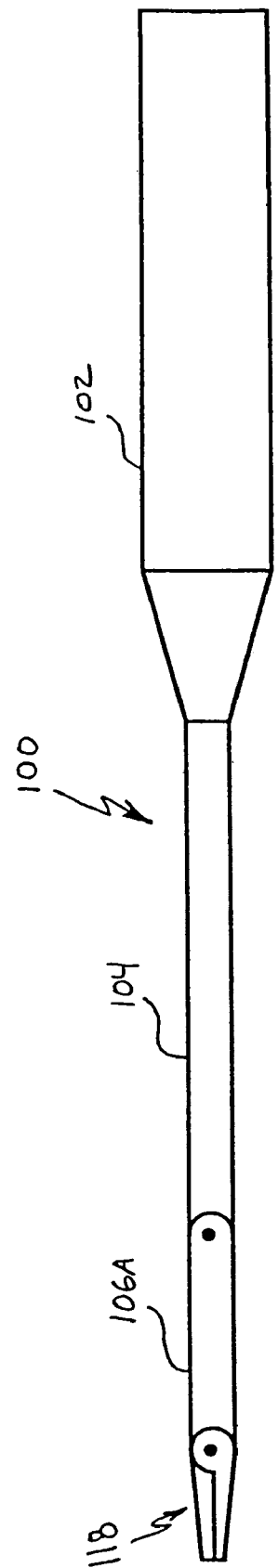
FIG. 23E is a side elevation view of an alternative embodiment of a positioning tool used in accordance with the present invention.

With reference also made to FIGS. 23A-C, a dissection and positioning tool 100 will now be described, in accordance with the present invention. As stated above, the dissection and positioning tool 100 allows a surgeon to gain access to, and further position medical instruments, such as the ablation system described herein, at various surgical sites throughout the body, especially during minimally invasive surgical procedures on the beating heart. More specifically, tool 100 further enables a surgeon to place the ablation device of an ablation instrument, or other medical instrument, adjacent to the outer surfaces of bodily structures along a predetermined lesion path, surrounding the structure for example. For illustration purposes only, the positioning tool 100 provides better access to the pulmonary truck and, more specifically, the individual pulmonary veins, during minimally invasive procedures facilitating placement of an ablation device adjacent to one or more pulmonary veins.

As shown in FIGS. 23A and 23B, positioning tool 100 comprises a handle 102 and a guide sheath 104 having a deflectable tip 106 operably attached to the distal end of sheath 104. Guide sheath 104 and tip 106 may be made from any suitable biocompatible material, such as those materials described herein with respect to sheath 52.

As will become readily apparent, an attachment point 108 may be utilized to permit the deflection of tip 106 along at least one plane allowing the distal end of tip 106 to more readily engage specific tissue at predetermined locations throughout the patients body. Attachment point 108 may be comprised of any suitable system allowing deflection of tip 106. For illustration purposes only, attachment point 108 may be formed by a matching node/recess pair. In this example, with reference also made to FIG. 23C, the distal end of sheath 104 comprises one or more nodes 114, preferably two, protruding from the external surface of the distal end of sheath 104. In turn, tip 106 comprises on or more matching recesses 116 which accept nodes 114 providing retention and holding tip 106 in a rotatably fixed position relative to sheath 104.

Alternatively, with reference to FIG. 23D, attachment point 108 could be achieved by one or more pins or rods passing through the distal portion of sheath 104 and the proximal portion of tip 106 at attachment point 108, defining a fulcrum about which tip 106 rotates. For example, attachment point 108 may comprise two rods 120, each passing through only the sheath 104 and tip 106 material, allowing for medical instruments to pass through sheath 104 and tip 106.

The tip portion 106 is deflectable with respect to sheath 104 through activation of a deflection means (not shown) as part of tool 100. FIGS. 23A & 23B depict tip 106 in an un-deflected and a deflected position, respectively, along one plane, with the distal end of tip 106 rotating about the attachment point 108 as indicated by arrow R. The deflection means may be any suitable means including, but not limited to, systems comprising one or more pull wires, springs of various shapes and configurations, sliders, switches, or motors, alone or in combination, allowing for the deflection of tip 106 in at least one plane. For example, tip 106 can be held in an un-deflected position relative to sheath 104 by a spring as part of a deflection means located at attachment point 108. Tension force applied to the distal end of tip 106, via one or more pull cables, overcomes the spring force and results in the deflection of tip 106. As the tension force is removed, the spring force acts to return tip 106 to its un-deflected position.

With reference also to FIG. 23C, tip 106 may be U-shaped along its longitudinal axis and may further comprise a retractable sharp distal tip 112 which further aides in dissection of bodily membranes, the pericardial reflection for example. While the distal tip 106 may be used to dissect or otherwise advance through tissue, sharp tip 112 encourages and assists with such advancement. For example, sharp tip 112 may assist in the dissection of the pericardial reflection allowing a medical instrument, ablation instrument 20 for example, to be positioned around the pulmonary veins for creation of a continuous transmural lesion, as described in more detail above. As should be readily understood, the recess defined by the U-shaped tip 106 acts to deflect medical instruments to facilitate proper placement with respect to a target tissue site. It should be apparent that if tool 100 is incorporated into and part of a medical instrument, as discussed in more detail below, tip 106 may comprise at least one lumen, accepting a slidably disposed medical instrument which passes from within sheath 104 and tip 106.

Deflectable tip 206 may also comprise an illumination means (not shown) operably attached to tip 206 such that light energy emitting therefrom aides in positioning of tip 206, especially during minimally invasive procedures. For example, when the tip 206 is advanced behind and around a bodily structure, the light energy provides an indication of where tip 206 is located. The illumination means may be any suitable source of light energy including, but not limited to, light emitting diodes, incandescent light sources, or any other sources which fluoresce and are compatible with corresponding light sensing systems utilized. The illumination means may provide light energy in the visible or non-visible range.

Sharp tip 112 is slidably disposed within tip 106 such that it can be retracted to a safe position when not in use. The tip 112 may be slidably affixed within the tip 106 itself or may be slidably attached to handle 102, passing through sheath 104 in an inner lumen (not shown) protecting the sheath 104 from sharp tip 112 translating therein. The tip 112 is controlled through any suitable activation means including, but not limited to, spring activated or pull wire systems. For example, tip 112 may be operably attached to a spring which, when triggered, allows for the instantaneous advancement of sharp tip 112 out from tip 106, the sharp tip 112 engaging adjacent tissue.

Alternatively, tip 112 activation means may be incorporated within or otherwise part of the deflection means of tip 106 described above. For illustration purposes only, the deflection means may comprise a slider in the handle portion operably attached to a pull wire and the tip 112. With the slider in a first position, the tip 106 is un-deflected and the sharp tip 112 is retracted to a point at least just within the distal end of tip 106. When the slider is advanced to a second position, the tip 106 is deflected such that the longitudinal axis of tip 106 defines a predetermined angle, indicated as arrow A in FIG. 23B, with the longitudinal axis of sheath 104. Finally, with the slider advanced to a third position, while the tip 106 remains rotatably fixed relative to the sheath 104, the sharp tip 112 may protrude from the distal end of the tip 106 a predetermined distance. In this way, the tip 106 of the tool 100 can be positioned at a predetermined location prior to activation of the sharp tip 112. The predetermined angle may be selected by a second slider, for example, such that operation of the tip 106, as discussed immediately above, may be performed in one controlled movement of the first slider.

The predetermined angle about which tip 106 is rotated with respect to sheath 104 can be any value between 0° and approximately 180°, 0° being defined as the angle A formed by the longitudinal axes of tip 106 and sheath 104 when tip 106 is in an un-deflected position, as shown in FIG. 23A. Further, it should be readily understood that tip 106 and sheath 104 can be of any suitable length with respect to each other allowing for differing configurations of tool 100 enabling tip 106 to engage tissue at any predetermined tissue site within a patient's body. Additionally, as should be readily apparent, sheath 104 may be slidably attached to handle 102 allowing for the extension and retraction of sheath 104 within handle 102 resulting in greater control over the placement of tip 106.

As is shown in FIGS. 23A and 23C, tip 106 may be formed having suitable dimensions allowing for passage of various medical instruments therethrough. Tip 106 may also include different geometric surfaces, such as lobe 110, which aide to move bodily structures away from sharp tip 112 as tip 106 is advanced and further provide clearance around the bodily structures for passage of the medical instrument. For example, after piercing of the pericardial reflection between a pulmonary vein and the superior vena cava, the tip 106 may be advanced, the lobe 110 slightly displacing the pulmonary vein allowing for passage of a medical instrument, such as ablation system 20.

Turning back to FIG. 21, in operation, tool 100 can be passed through access port 87A (not shown) and advanced into the body. As discussed above, the tool 100 is manipulated to position the distal tip 106 at a predetermined location and orientation within the body to facilitate positioning of a medical instrument system, such as an ablation system, at a target tissue site. The target tissue site may comprise, for example, a circumferential portion of the external surface of a biological structure, the heart for example.

Additionally, if applicable, tool 100 is manipulated until the distal tip 106 nears or engages tissue to be dissected. At this point tip 106 is positioned at a predetermined angle with respect to sheath 104 and is proximate to the tissue. Sharp tip 112 is then advanced passed the distal end of tip 106 engaging the tissue and creating an opening therethrough. Once the opening is created, tool 100 can be retracted and the medical instrument system advanced therethrough allowing access to target tissue sites beyond the dissected tissue. The medical instrument system, for example, may be an ablation system as described herein which can be passed therethrough and further advanced along an ablation path.

As should be readily apparent, the functionality of tool 100 can be incorporated into the ablation system 20 itself. For example, tip 106 may be attached to the distal end of guide sheath 52, in a manner described above. In this configuration, tip 106 would act to further deflect or otherwise direct the ablation sheath which passes therethrough such that at least a portion of the ablation element of the ablation system is deflected and positioned at a desired target tissue site. Alternatively, with reference to FIG. 24, the deflectable tip can be integral to the guide sheath itself.

Figure 24:
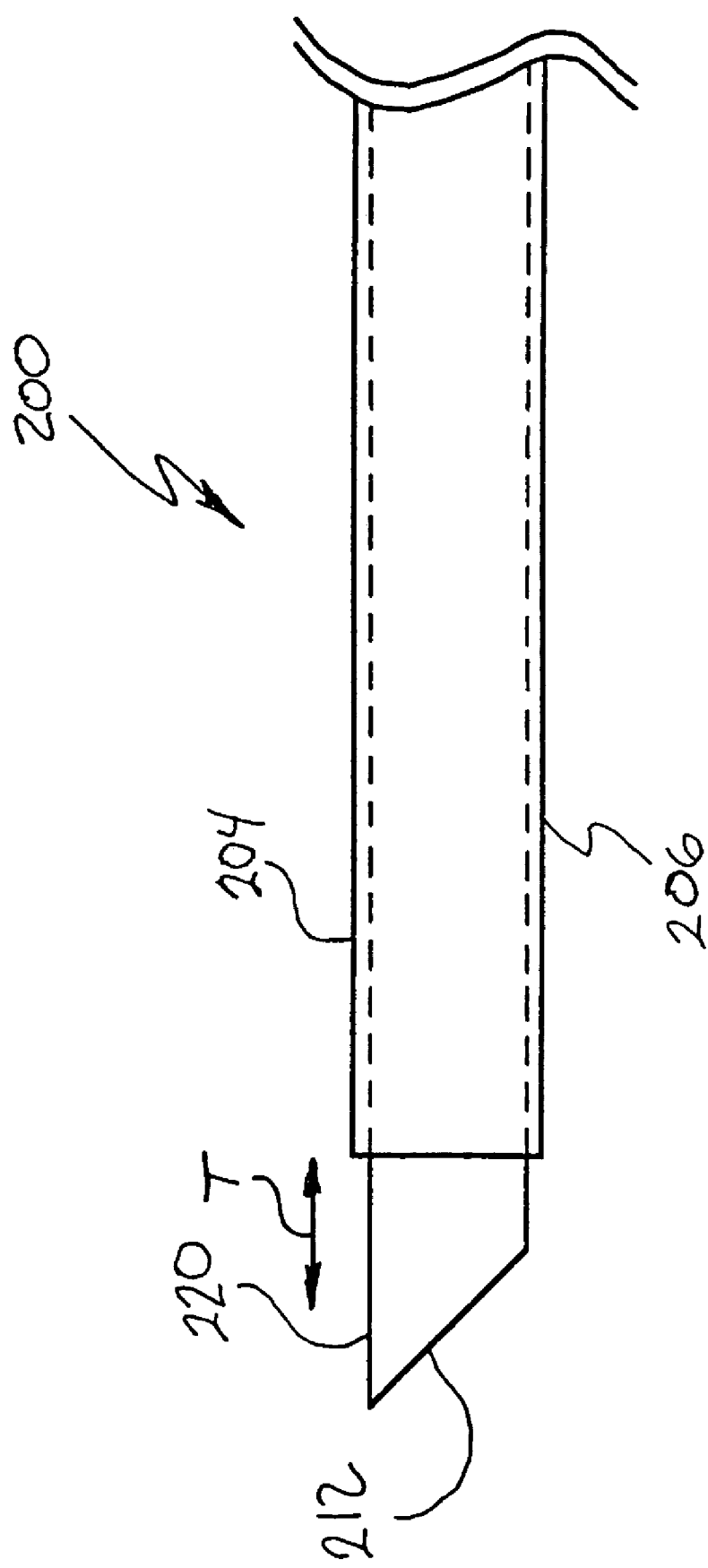
FIG. 24 is a side view of another alternative embodiment of a positioning tool used in accordance with the present invention.

FIG. 24 depicts tool 200 comprising a guide sheath 204 having at least one lumen and a deflectable tip 206, and an inner sheath 220 slidably disposed within the at least one lumen of sheath 204. Sheath 204 has at least one lumen passing therethrough and an angled needle tip 212 at its distal end. The medical instrument, ablation system 20 for example, is slidably disposed within the at least one lumen of inner sheath 220. In operation, as with tool 100, tool 200 is first advanced within a patient's body, the deflectable tip 206 being positioned adjacent a target tissue site. In this way the medical instrument can be slidably advanced through the inner sheath 220, at least a portion of the medical instrument being deflected and positioned adjacent to the target tissue site.

As with the sharp tip 112 of tool 100, inner sheath 220 can be translated within inner sheath 220 such that the distal end of needle tip 212 passes through the distal opening of deflectable tip 206, engaging and penetrating tissue to be dissected and creating an opening therethrough for at least a portion of the medical instrument to pass. The needle tip 212 of the inner sheath 220 is angled in such a way as to encourage the creation of an opening in the tissue, rather than removal of the tissue itself. As with the tool 100 embodiments above, the deflectable tip 206 may act to deflect and position the medical instrument such that at least a portion of the medical instrument is adjacent to a target tissue site.

Furthermore, it should be understood that tool 100, 200 may be utilized with any ablation system, as a separate tool or as part of the ablation system itself. For example, tool 100, 200 could be used along with or as part of the ablation instrument as described in U.S. patent application No. 09/474,548, now issued as U.S. Pat. No. 7,033,352, which is incorporated herein by reference, in its entirety.

Now with reference to FIG. 23D, another embodiment of the dissection and positioning tool 100 is depicted having an alternate tip 106A. Tip 106A comprises a grasping means 118 at its distal end. Grasping means 118 allows a surgeon to grasp a surgical instrument during operative procedures enabling the surgeon to place the surgical instrument adjacent to the outer surfaces of bodily structures, surrounding the structure for example.

For illustration purposes only, the positioning tool 100 as depicted in FIG. 23D may be passed through the pericardial reflection from an inferior vena cava access point, as discussed above. Once the tip 106A passes through the pericardial reflection, the grasping means 118 would then grasp the distal tip of a medical instrument, such as the ablation system 20, and retract the instrument, further guiding and positioning the instrument adjacent to the pulmonary trunk, from the transverse sinus to the inferior pulmonary vein sinus and finally back out to the inferior vena cava access point.

More specifically, the distal end of ablation system 20, such as the ablation guide 22 for example, incorporates a grasping surface (not shown) suitable for grasping by grasping means 118. The distal tip of tool 100 is passed through the pericardial reflection as described above, and the grasping means 118 as part of the tip 106A grasps or otherwise engages and holds onto the grasping surface. The tool 100 is then retracted along with the ablation guide 22, back out the inferior vena cava access point resulting in the proper positioning of the ablation guide 22 and, ultimately, the ablation device 26 slidably disposed therein. Once positioned, tissue ablation occurs as described in greater detail above.

The grasping means can be any suitable means compatible with the medical instrument. For example, the distal end of the instrument may comprise an opening allowing for placement of a suture thereon. The grasping means 118 of tool 100 as part of tip 106A may be in the form of a pair of pivoted jaws 120, at least one of the jaws being movable with respect to the other enabling the jaws 120 to close upon the suture, grasping or otherwise holding onto the suture for retraction by tool 100 as described above. The pivot point of the pivoted jaws 120 may form part of attachment point 108 as described above.

Alternatively, the grasping means 118 may be in the form of a hook and loop system (not shown), the hook disposed on the distal end of tip 106A and the loop formed as a structural part of the distal end of the ablation device or formed with a suture as described immediately above. Additionally, tip 106 may further comprise a blunt barb (not shown) for grasping a suture or other loop as part of the distal end of an ablation device allowing for retraction of the ablation device as discussed above.

In accordance with yet another aspect of the present invention, the guide sheath, or ablation sheath, or ablation element could be controlled by a robot during a robotic minimally invasive surgical procedure. The robot could indeed telescopically translate or rotate the guide sheath, or the ablation sheath, or the ablation element in order to position the ablation sheath and the ablation element correctly to produce the ablation of tissue. The robot could also perform other tasks to facilitate the access of the ablation sheath to the tissue to be ablated. These tasks include, but are not limited to: performing the pericardial reflection in the area of a pulmonary vein; performing an incision on the pericardial sac; manipulating, bending or shaping the ablation sheath; or performing an incision on an organ to penetrate the ablation sheath through the penetration hole.

In accordance with yet another aspect of the present invention, the concept of using a sliding ablation element in an ablation sheath to ablate from the epicardium of a beating heart can also be applied in open chest surgery. In this procedure, a malleable ablation sheath may be beneficial, as compared to a pre-shaped ablation sheath. For example, a malleable metallic wire (e.g., copper, stainless steel, etc. . . . ) could be integrated into the ablation sheath. The cardiac surgeon will then shape the ablation sheath to create the ablation path that he wants and will finally produce the ablation line by overlapping several ablations In this technique, it is important to note that the ablation sheath must be stabilized against the epicardium since the ablation sheath will define the ablation path of the energy delivery portion. Should the ablation sheath be inadvertently moved during the process, the final ablation line may be undesirably discontinuous. Thus, a securing device may be applied to secure the ablation sheath against the epicardium. Such a securing device may include stitches or the like which may be strung through receiving holes or cracks placed in the ablation sheath. Another device to anchor the ablation sheath to the epicardium may be in the form of a biocompatible adhesive, or a suction device.

In accordance with yet another aspect of the present invention, a way to visually locate the ablation element within the ablation sheath is provided to the surgeon. In one embodiment of the invention, the ablation sheath is transparent and the ablation element can be directly visualized, or indirectly visualized via an endoscope. In yet another embodiment of the application, a marking element that can be directly visually identify along the ablation sheath, or indirectly visualized via an endoscope, is used to identify the location of the ablation element within the sheath. The marking element is sliding with the ablation element to show the location of the ablation element.

In accordance with yet another aspect of the present invention, a way to indirectly locate the ablation element within the ablation sheath is provided to the surgeon. A position finding system is incorporated in the handle of the device to indicate the position of the ablation element within the ablation sheath. At least one marker can be directly visually, or indirectly visually identified. These markers can be used in collaboration with the position finding system as reference points to identify the location of the ablation element.

While the present invention has been primarily described and applied for epicardial tissue ablations, it will be appreciated that the ablation system 20 may just as easily apply to endocardial tissue ablations as well. The tissue ablations may be performed through either open surgery techniques or through minimal invasive techniques.

Although the foregoing invention has been described in some detail for purposes of clarity of understanding, it will be apparent that certain changes and modifications may be practiced within the scope of the appended claims.

What is claimed is:

1. A method of positioning a medical instrument within a patient's body using a guide sheath having a sharp tip at a deflectable distal end during a surgical procedure, comprising the steps of:

introducing into the patient's body the guide sheath having the deflectable distal end and having a longitudinal axis and at least one lumen passing therethrough that is aligned along the longitudinal axis near the distal end;

dissecting tissue with the sharp tip;

deflecting the deflectable distal end of the sheath within the patient's body;

introducing the medical instrument into the guide sheath positioned within the patient's body toward a target tissue site; and advancing the distal end of the medical instrument through the at least one lumen to the deflectable distal end thereof for positioning at least a portion of the medical instrument within the deflected distal end of the guide sheath near the target tissue site.

2. The method of claim 1 wherein deflecting the deflectable distal end includes deflecting by an angular amount skewed from the longitudinal axis of about 180°.

3. The method of claim 1 wherein dissecting tissue comprises advancing the sharp tip to extend distally past the deflectable distal end.

4. The method of claim 1 wherein the medical instrument includes a tissue-ablating element and the method further comprises positioning the tissue-ablating element within the deflectable distal end.

* * * * *